(12) United States Patent
Ito et al.

(10) Patent No.: US 10,975,396 B2
(45) Date of Patent: Apr. 13, 2021

(54) D-GLUCARIC ACID PRODUCING BACTERIUM, AND METHOD FOR MANUFACTURING D-GLUCARIC ACID

(71) Applicants: Ensuiko Sugar Refining Co., Ltd., Tokyo (JP); Osaka Research of Industrial Science and Technology, Osaka (JP)

(72) Inventors: Tetsuya Ito, Tokyo (JP); Hiroki Tadokoro, Tokyo (JP); Hisaharu Masaki, Tokyo (JP); Katsuhiko Mikuni, Tokyo (JP); Hiromi Murakami, Osaka (JP); Taro Kiso, Osaka (JP); Takaaki Kiryu, Osaka (JP)

(73) Assignees: Ensuiko Sugar Refining Co., Ltd., Tokyo (JP); Osaka Research Institute of Industrial Science and Technology, Osaka (JP)

(*) Notice: Subject to any disclaimer, the term of this patent is extended or adjusted under 35 U.S.C. 154(b) by 141 days.

(21) Appl. No.: 14/404,714

(22) PCT Filed: Jun. 3, 2013

(86) PCT No.: PCT/JP2013/065414
§ 371 (c)(1),
(2) Date: Dec. 1, 2014

(87) PCT Pub. No.: WO2013/183610
PCT Pub. Date: Dec. 12, 2013

(65) Prior Publication Data
US 2015/0152448 A1 Jun. 4, 2015

(30) Foreign Application Priority Data
Jun. 4, 2012 (JP) .............................. JP2012-127467

(51) Int. Cl.
| | |
|---|---|
| *C12P 7/58* | (2006.01) |
| *C12P 7/24* | (2006.01) |
| *C12P 19/00* | (2006.01) |
| *C12N 9/04* | (2006.01) |
| *C12N 9/02* | (2006.01) |
| *C12P 7/42* | (2006.01) |
| *C12N 15/09* | (2006.01) |
| *C12N 1/20* | (2006.01) |

(52) U.S. Cl.
CPC .................. *C12P 7/58* (2013.01); *C12N 1/20* (2013.01); *C12N 9/0006* (2013.01); *C12N 9/0008* (2013.01); *C12N 15/09* (2013.01); *C12P 7/24* (2013.01); *C12P 7/42* (2013.01); *C12P 19/00* (2013.01)

(58) Field of Classification Search
CPC ........ C12N 15/09; C12N 1/20; C12N 9/0006; C12N 9/0008; C12P 7/24; C12P 19/00; C12P 7/42; C12P 7/58
See application file for complete search history.

(56) References Cited

U.S. PATENT DOCUMENTS

| | | | |
|---|---|---|---|
| 2,436,659 | A | 2/1948 | Mehltretter |
| 2,472,168 | A | 6/1949 | Mehltretter et al. |
| 4,876,195 | A | 10/1989 | Shirafuji et al. |
| 5,437,989 | A | 8/1995 | Asakura et al. |
| 5,599,977 | A | 2/1997 | Kiely et al. |
| 6,498,269 | B1 | 12/2002 | Merbouh et al. |
| 7,692,041 | B2 | 4/2010 | Kiely et al. |
| 8,530,186 | B2 | 9/2013 | Ito et al. |
| 2010/0075381 | A1 | 3/2010 | Ito et al. |
| 2011/0124065 | A1 | 5/2011 | Moon et al. |

FOREIGN PATENT DOCUMENTS

| | | |
|---|---|---|
| JP | 62-228287 | 10/1987 |
| JP | 05-068542 | 3/1993 |
| JP | 07-000182 | 1/1995 |
| JP | 2003-159079 | 6/2003 |
| JP | 3713530 B2 | 11/2005 |
| JP | 2011-516063 A | 5/2011 |
| WO | 2002074926 A2 | 9/2002 |
| WO | 2008139844 A1 | 11/2008 |

(Continued)

OTHER PUBLICATIONS

Adachi et al., New Developments in Oxidative fermentation, Appl. Microbiol. Biotechnol. (2003) 60: 643-653.*

(Continued)

*Primary Examiner* — Susan M Hanley
(74) *Attorney, Agent, or Firm* — Suzannah K. Sundby, Esq.; Canady + Lortz LLP

(57) ABSTRACT

The present invention provides a D-glucaric acid-producing bacterium and a method for producing D-glucaric acid. The present invention is characterized in that D-glucaric acid or a salt thereof is produced from one or more saccharides selected from the group consisting of D-glucose, D-gluconic acid and D-glucuronic acid with catalytic action of a specific alcohol dehydrogenase PQQ-ADH (1) and a specific aldehyde dehydrogenase PQQ-ALDH (2), and that D-glucaric acid or a salt thereof is produced by using a microorganism having the PQQ-ADH (1) and the PQQ-ALDH (2) or a processed product thereof in the presence of the one or more saccharides. The present invention can provide a microorganism having improved productivity of D-glucaric acid to be used for production of D-glucaric acid and a method for efficiently producing D-glucaric acid.

8 Claims, 17 Drawing Sheets
Specification includes a Sequence Listing.

(56) References Cited

FOREIGN PATENT DOCUMENTS

| WO | WO 2008139844 | * 11/2008 | ............... C12N 1/20 |
|---|---|---|---|
| WO | 2009145838 A2 | 12/2009 | |

OTHER PUBLICATIONS

Werpy & Petersen, "Top value added chemicals from biomass", "vol. 1: Results of screening for potential candidates from sugars and synthesis gas", Aug. 2004, Publisher: U.S. Department of Energy.
Moon, et al., "Use of modular, synthetic scaffolds for improved production of glucaric acid in engineered *E. coli*", Feb. 1, 2010, pp. 298-305, vol. 12, No. 3, Publisher: Metabolic Engineering.
Harold Roper, "Selective Oxidation of D-Glucose Chiral Intermediates for Industrial Utilization", 1990, pp. 342-349, vol. 42, No. 9, Publisher: Starch.
Walaeszek, "Coordinated Review Letters: The Prevention of Cancer", "Potential use of D-glucaric acid derivatives in cancer prevention", 1990, pp. 1-8, vol. 54, Publisher: Cancer Letters.
Office Action received in AU 2013272645 dated Apr. 30, 2018.
First Office Action received in CN 201380029481 dated Dec. 30, 2016 (translation from Global Dossier).
Second Office Action received in CN 201380029481 dated Sep. 11, 2017 (translation from Global Dossier).
Third Office Action received in CN 201380029481 dated Mar. 15, 2018 (machine translation).
Fourth Office Action received in CN 201380029481 dated Sep. 25, 2018 (machine translation).
Notification of Reasons for Refusal received in JP 2014-519991 dated Feb. 24, 2017 (translation from Global Dossier).
Decision of Refusal received in JP 2014-519991 dated Oct. 30, 2017 (translation from Global Dossier).

* cited by examiner

[SEQ ID No. 1]

```
1    ATG CTG AAA CAA AGC CTG TTA GCA TCA GGT TTA GCG GCG CTC TGT GTC GCC GCC ATG GGC   60
1    Met Leu Lys Gln Ser Leu Leu Ala Ser Gly Leu Ala Ala Leu Cys Val Ala Ala Met Gly   20

61   AGC TTG TCG CTG GCT GCC GAA ACG ACG AGC GAG CGC CTG CTC AAT GCC GGC AGC GAG GCC  120
21   Ser Leu Ser Leu Ala Ala Glu Thr Thr Ser Glu Arg Leu Leu Asn Ala Gly Ser Glu Ala   40

121  GAG AAT GGC AAC TGG CTC ATG GTG CAC CGC ACC TAT GAC AGC CAT CGC TTC AGC CCG CTC  180
41   Glu Asn Gly Asn Trp Leu Met Val His Arg Thr Tyr Asp Ser His Arg Phe Ser Pro Leu   60

181  TCC GAG ATC AAC AAG GAC ACC ATC AAG GAC CTT GGC CTG GCC TCC GTG ACC ATT CTG GAT  240
61   Ser Glu Ile Asn Lys Asp Thr Ile Lys Asp Leu Gly Leu Ala Ser Val Thr Ile Leu Asp   80

241  AAT GCC TCG CGC GGC GGC CGC TAT GCC AGC GCC CGC AAC GAA GGC ACG CCG CTG GTC GAA  300
81   Asn Ala Ser Arg Gly Gly Arg Tyr Ala Ser Ala Arg Asn Glu Gly Thr Pro Leu Val Glu  100

301  GAC GGC TTC ATG TAC CTG CAA TCC GGC TGG TCC GTA GTC TAT AAG CTC GAC GTC CGC GAC  360
101  Asp Gly Phe Met Tyr Leu Gln Ser Gly Trp Ser Val Val Tyr Lys Leu Asp Val Arg Asp  120

361  GGC AAG ACC GCC AAG GTG GTC TGG AAG TAC GAT CCG GAA GTC GAT CGC CAG TGG GTT TCC  420
121  Gly Lys Thr Ala Lys Val Val Trp Lys Tyr Asp Pro Glu Val Asp Arg Gln Trp Val Ser  140

421  GAC GCC ACC TGC TGC GGC GCC GAG AAC CGC GGT ATC GGC CTG TGG AAC GAC GAC GTG GTc  480
141  Asp Ala Thr Cys Cys Gly Ala Glu Asn Arg Gly Ile Gly Leu Trp Asn Asp Asp Val Val  160

481  GCC CTG ACC ATG GAT GGC CGC GTC ATG TCC ATC AAC AAG GAC ACC GGC GAG CTC AAC TGG  540
161  Ala Leu Thr Met Asp Gly Arg Val Met Ser Ile Asn Lys Asp Thr Gly Glu Leu Asn Trp  180

541  GAA AAG CAG CG GCT GAC AAG GCG CGT GCC GAA AGC TTC ACC GGC GCC CCG CTC ATC ATC  600
181  Glu Lys Gln Arg Ala Asp Lys Ala Arg Ala Glu Ser Phe Thr Gly Ala Pro Leu Ile Ile  200

601  GGC GAC ACC GCC GTT TAT GGT CCG GCT GGT GGC GAA TAC GGC ATC CGC GGC TGG CTC GAA  660
201  Gly Asp Thr Ala Val Tyr Gly Pro Ala Gly Gly Glu Tyr Gly Ile Arg Gly Trp Leu Glu  220

661  GCC ATC GAC CTC AAG ACC GGC GAT GTG GCC TGG CGT ACC TAT ACC GTG CCC GGA CCG GGC  720
221  Ala Ile Asp Leu Lys Thr Gly Asp Val Ala Trp Arg Thr Tyr Thr Val Pro Gly Pro Gly  240

721  GAG CCC GGC AAT GAT ACC TGG CAG GGC AAT GCC TGG GAA ACC GGC GGC GCT TCC ATC TGG  780
241  Glu Pro Gly Asn Asp Thr Trp Gln Gly Asn Ala Trp Glu Thr Gly Gly Ala Ser Ile Trp  260

781  CAG ACG GGT TCC TAC GAC CCC GAT ACC GGC ATG ACC TAT TGG GGC ACG GGT AAC CCG GCT  840
261  Gln Thr Gly Ser Tyr Asp Pro Asp Thr Gly Met Thr Tyr Trp Gly Thr Gly Asn Pro Ala  280

841  CCG CAG ATC GAC GCC GAA TAC CGT CCG GGC GAC AAC CTC TAT GCT TCG AGC CTG CTC GCG  900
281  Pro Gln Ile Asp Ala Glu Tyr Arg Pro Gly Asp Asn Leu Tyr Ala Ser Ser Leu Leu Ala  300
```

Fig. 11

[SEQ ID No.1] (be continued)

```
901  CTC GAC GCC AAG GAT GGT GCT CTC AAG TGG CAC TTC CAG TTC ACC CCG AAC GAT CCG TAC  960
301  Leu Asp Ala Lys Asp Gly Ala Leu Lys Trp His Phe Gln Phe Thr Pro Asn Asp Pro Tyr  320

961  GAC TAT GAC GAA ATC GGC GAC AAC CAG CTC CTG GAT GTG AGC GTG GAT GGC AAG CCG TCC  1020
321  Asp Tyr Asp Glu Ile Gly Asp Asn Gln Leu Leu Asp Val Ser Val Asp Gly Lys Pro Ser  340

1021 AAG ATG GTC GTC CGC GCT GCC CGT AAC GGT TTC ATG TAT GGC TTC AAC CGT CTC GAC GGC  1080
341  Lys Met Val Val Arg Ala Ala Arg Asn Gly Phe Met Tyr Gly Phe Asn Arg Leu Asp Gly  360

1081 GCC ATG ACC TAT GCC AAG CAG TAT GTG GAA GAC CTG ACC TGG ACC ACC GGC ATC GAC CCG  1140
361  Ala Met Thr Tyr Ala Lys Gln Tyr Val Glu Asp Leu Thr Trp Thr Thr Gly Ile Asp Pro  380

1141 AAG ACC GGC AAG CCG CTC GAA TAC GAT CCG AAG GCC CAG CTC CAG AAG TAC GTC GCC GGC  1200
381  Lys Thr Gly Lys Pro Leu Glu Tyr Asp Pro Lys Ala Gln Leu Gln Lys Tyr Val Ala Gly  400

1201 ACC GTT GGC TCG CGT GAA GGC AAT CCG GGC ATC TAC TGC CCG ACG CTG GGT GGC GGC AAG  1260
401  Thr Val Gly Ser Arg Glu Gly Asn Pro Gly Ile Tyr Cys Pro Thr Leu Gly Gly Gly Lys  420

1261 AAC TGG CAG CCT GCT GCC TAT AGC CCG AAC ACC AAG CTC CTC TAC GTG ACC TCG GCT GAA  1320
421  Asn Trp Gln Pro Ala Ala Tyr Ser Pro Asn Thr Lys Leu Leu Tyr Val Thr Ser Ala Glu  440

1321 GGC TGC TCG GCC TAT GTG CCC GAG GCT GCT CCC AAT CCG ACG ACC ACC GGC GGT GAA TAC  1380
441  Gly Cys Ser Ala Tyr Val Pro Glu Ala Ala Pro Asn Pro Thr Thr Thr Gly Gly Glu Tyr  460

1381 GAC GTG GTC AAG GCT CAG CGC GAA TGG AAC GGC CGT CTG CCG GCT CCT GAA GGC ACC AAG  1440
461  Asp Val Val Lys Ala Gln Arg Glu Trp Asn Gly Arg Leu Pro Ala Pro Glu Gly Thr Lys  480

1441 CTG CCG GAC GTC TTC AAC GGC GGC TCG GTG AAG GCC ATC GAC CCG CTC ACC GGC GAA ACC  1500
481  Leu Pro Asp Val Phe Asn Gly Gly Ser Val Lys Ala Ile Asp Pro Leu Thr Gly Glu Thr  500

1501 AAG GCC AAG GTC CTG GTG CCC CGC CGC CTG AAC GGC ATG CTC GCC ACC GGT GGC GAC CTG  1560
501  Lys Ala Lys Val Leu Val Pro Arg Arg Leu Asn Gly Met Leu Ala Thr Gly Gly Asp Leu  520

1561 GTC TGG AGC TCG GGC ACG GAT GGT AAC CTC TAT GCC TAT GAC GCC AAC ACT CTG GAA ACC  1620
521  Val Trp Ser Ser Gly Thr Asp Gly Asn Leu Tyr Ala Tyr Asp Ala Asn Thr Leu Glu Thr  540

1621 GTG TGG ACC TTC AAC GTC GGC ACC GCC CTT GGT GGC CCG CCG ATG AGC TAC TCG GTC GAC  1680
541  Val Trp Thr Phe Asn Val Gly Thr Ala Leu Gly Gly Pro Pro Met Ser Tyr Ser Val Asp  560

1681 GGC AAG CAG TAC GTC GCG GTT CTC GCC GGT GCT GCC GCC TCC GCT GCC GAC AAG AAG GTT  1740
561  Gly Lys Gln Tyr Val Ala Val Leu Ala Gly Ala Ala Ala Ser Ala Ala Asp Lys Lys Val  580

1741 GCG CCG CAG TCC GAG TTC TTC GTG CCG GCT GAT GCG CTC TAC ATC TTC GCG CTG AAG TAA  1800
581  Ala Pro Gln Ser Glu Phe Phe Val Pro Ala Asp Ala Leu Tyr Ile Phe Ala Leu Lys End  599
```

Fig 12

[SEQ ID No. 2]

| | | | | | | | | | | | | | | | | | | | | | |
|---|---|---|---|---|---|---|---|---|---|---|---|---|---|---|---|---|---|---|---|---|---|
| 1 | ATG | TAC | AGG | AAA | GGC | AGT | GTG | CTG | ACC | GTG | TCA | GCA | CTC | GTC | TTG | GGG | CTT | TGC | ACA | TCG | 60 |
| 1 | Met | Tyr | Arg | Lys | Gly | Ser | Val | Leu | Thr | Val | Ser | Ala | Leu | Val | Leu | Gly | Leu | Cys | Thr | Ser | 20 |
| 61 | TCT | GTG | TGG | GCC | CAG | CAG | GCG | CCG | ACG | ACC | AAC | GCT | CTC | GAC | AAC | CTC | ACT | CCC | GTC | ACC | 120 |
| 21 | Ser | Val | Trp | Ala | Gln | Gln | Ala | Pro | Thr | Thr | Asn | Ala | Leu | Asp | Asn | Leu | Thr | Pro | Val | Thr | 40 |
| 121 | GAC | GAC | GTT | CTC | AAG | AAC | CCT | GCC | GAT | GGC | GAC | TGG | CTG | ATG | GCC | CGC | CGA | ACT | TAT | AAC | 180 |
| 41 | Ser | Val | Trp | Ala | Gln | Gln | Ala | Pro | Thr | Thr | Asn | Ala | Leu | Asp | Asn | Leu | Thr | Pro | Val | Thr | 60 |
| 181 | GGC | TGG | GGC | TAC | AGC | CCC | CTC | GAT | CAG | ATC | AAC | AAG | GAC | AAC | GTC | GAC | AAG | CTT | CAA | CTC | 240 |
| 61 | Gly | Trp | Gly | Tyr | Ser | Pro | Leu | Asp | Gln | Ile | Asn | Lys | Asp | Asn | Val | Asp | Lys | Leu | Gln | Leu | 80 |
| 241 | GTT | TGG | TCG | TGG | GGT | CTG | TCA | CCC | GGC | GGC | ACG | ACG | CAG | GAG | ACG | CCG | CTC | GTT | CAT | GAT | 300 |
| 81 | Val | Trp | Ser | Trp | Gly | Leu | Ser | Pro | Gly | Gly | Thr | Thr | Gln | Glu | Thr | Pro | Leu | Val | His | Asp | 100 |
| 301 | GGC | GTC | ATG | TTC | GTT | CAG | AAT | TCG | AGC | CAC | CTC | ATT | CAG | GCG | CTC | GAT | GCG | GGC | ACT | GGC | 360 |
| 101 | Gly | Val | Met | Phe | Val | Gln | Asn | Ser | Ser | His | Leu | Ile | Gln | Ala | Leu | Asp | Ala | Gly | Thr | Gly | 120 |
| 361 | GAA | CTG | CTG | TGG | CAG | TAC | CAG | TAT | TCC | CTC | CCC | ACC | GGC | GTC | AAT | CCG | GCC | GGC | CAG | CGC | 420 |
| 121 | Glu | Leu | Leu | Trp | Gln | Tyr | Gln | Tyr | Ser | Leu | Pro | Thr | Gly | Val | Asn | Pro | Ala | Gly | Gln | Arg | 140 |
| 421 | TCC | AAG | GCG | CTC | TAT | GGT | GAC | AAC | CTG | ATC | TTT | GCG | ACC | CGC | GAT | GCC | CAT | ATC | GTC | GCC | 480 |
| 141 | Ser | Lys | Ala | Leu | Tyr | Gly | Asp | Asn | Leu | Ile | Phe | Ala | Thr | Arg | Asp | Ala | His | Ile | Val | Ala | 160 |
| 481 | GTC | AAC | GCC | AAG | ACC | GGC | AAG | CTG | GCC | TGG | GAC | CAG | CAG | GTC | GCC | GAC | TAC | AAG | AAG | GGC | 540 |
| 161 | Val | Asn | Ala | Lys | Thr | Gly | Lys | Leu | Ala | Trp | Asp | Gln | Gln | Val | Ala | Asp | Tyr | Lys | Lys | Gly | 180 |
| 541 | TGG | GGC | TAT | TCC | TCG | GGG | CCG | CTG | GTA | GCC | GAC | GGC | ACC | ATC | ATC | CAG | GGC | ATG | ACC | AAT | 600 |
| 181 | Trp | Gly | Tyr | Ser | Ser | Gly | Pro | Leu | Val | Ala | Asp | Gly | Thr | Ile | Ile | Gln | Gly | Met | Thr | Asn | 200 |
| 601 | TGC | GGC | AAC | GGC | GAA | CCC | GGC | GGC | TGC | TTC | ATC | ACC | GGC | CAC | GAC | CCA | GCG | ACC | GGT | AAG | 660 |
| 201 | Cys | Gly | Asn | Gly | Glu | Pro | Gly | Gly | Cys | Phe | Ile | Thr | Gly | His | Asp | Pro | Ala | Thr | Gly | Lys | 220 |
| 661 | GAA | TTG | TGG | CGG | CTC | AAC | ACC | ATC | GCG | TCC | GGC | GAC | ACG | CCC | GAA | GGC | AAT | AGC | TGG | AAC | 720 |
| 221 | Glu | Leu | Trp | Arg | Leu | Asn | Thr | Ile | Ala | Ser | Gly | Asp | Thr | Pro | Glu | Gly | Asn | Ser | Trp | Asn | 240 |
| 721 | GGC | CTG | CCG | CAG | ATG | TCG | CGC | TAT | GGC | GCT | TCG | GCC | TGG | ATC | ACC | GGC | TCC | TAC | GAT | CCC | 780 |
| 241 | Gly | Leu | Pro | Gln | Met | Ser | Arg | Tyr | Gly | Ala | Ser | Ala | Trp | Ile | Thr | Gly | Ser | Tyr | Asp | Pro | 260 |
| 781 | GAC | CAG | AAC | ATC | GTC | TTC | GCC | GGC | GTC | GGC | CAG | CCG | TAT | CCG | TGG | CCG | GCG | GTG | TTG | AAC | 840 |
| 261 | Asp | Gln | Asn | Ile | Val | Phe | Ala | Gly | Val | Gly | Gln | Pro | Tyr | Pro | Trp | Pro | Ala | Val | Leu | Asn | 280 |
| 841 | GGG | CTT | CTC | CCG | AAG | AGC | ACG | GAT | TCG | AAG | TAC | ACC | AAC | AAT | GCG | GCT | TAT | ACC | GAT | TCC | 900 |
| 281 | Gly | Leu | Leu | Pro | Lys | Ser | Thr | Asp | Ser | Lys | Tyr | Thr | Asn | Asn | Ala | Ala | Tyr | Thr | Asp | Ser | 300 |

Fig. 13

[SEQ ID No.2] (be continued)

```
 901 ACG CTG GCG ATC GAG CCG AAG ACC GGC GCG CTG AAG TGG TAT GAT CAG TAC CTG GCC ACG  960
 301 Thr Leu Ala Ile Glu Pro Lys Thr Gly Ala Leu Lys Trp Tyr His Gln Tyr Leu Ala Thr  320

961 GAT ACG CTC GAC CTC GAC TAT GTG TAT GAG CGT CTG CTC GTC GAT CTG CCC GTC AAG GGC 1020
 321 Asp Thr Leu Asp Leu Asp Tyr Val Tyr Glu Arg Leu Leu Val Asp Leu Pro Val Lys Gly  340

1021 GAG GCG ACC AAG CAG GTG ATT ACT GCC GGC AAG CTC GCC ATC ATC GAG TCG CTC GAC CGG 1080
 341 Glu Ala Thr Lys Gln Val Ile Thr Ala Gly Lys Leu Ala Ile Ile Glu Ser Leu Asp Arg  360

1081 ACC TCG GGC AAG TGG CTC TGG GCG CAC GAA ACG GTA CCG CAG AAC GTG GTG TCG GCC ATC 1140
 361 Thr Ser Gly Lys Trp Leu Trp Ala His Glu Thr Val Pro Gln Asn Val Val Ser Ala Ile  380

1141 GAT CCG GTC ACC GGC GAG AAG ACC ATC AAT CCC GAT GTG ATC CCG CAG GTG GGC AAG ACC 1200
 381 Asp Pro Val Thr Gly Glu Lys Thr Ile Asn Pro Asp Val Ile Pro Gln Val Gly Lys Thr  400

1201 ACG GTC AAC TGC CCT GCC GAC CCG GGC GGC CGC GCC TGG CAG GCG ACT TCG TTC AGC CCG 1260
 401 Thr Val Asn Cys Pro Ala Asp Pro Gly Gly Arg Ala Trp Gln Ala Thr Ser Phe Ser Pro  420

1261 AAG ACG CAA ATG ATG TAT ATG CCC ACT GTC GAG TTC TGC TCG AAT ACC GAC GTC AAC CCG 1320
 421 Lys Thr Gln Met Met Tyr Met Pro Thr Val Glu Phe Cys Ser Asn Thr Asp Val Asn Pro  440

1321 CTC GAT CCG GGC CAG GTC TAT ACC GGT GGC GGT CTT GCG ACC TTC AAC CGC GTG CCG CGG 1380
 441 Leu Asp Pro Gly Gln Val Tyr Thr Gly Gly Gly Leu Ala Thr Phe Asn Arg Val Pro Arg  460

1381 CCG GAT AGC GAT GGC AAT ATC GGT CAG GTG CGC GCC ATC AAT CTT GCC GAC CAG ACG GAT 1440
 461 Pro Asp Ser Asp Gly Asn Ile Gly Gln Val Arg Ala Ile Asn Leu Ala Asp Gln Thr Asp  480

1441 GCC TGG ATG TAT CGC CAG CAC GCT CCG GTC ACC ACC TCG ACG CTG CCG ACC GGT GGC GGC 1500
 481 Ala Trp Met Tyr Arg Gln His Ala Pro Val Thr Thr Ser Thr Leu Pro Thr Gly Gly Gly  500

1501 CTG GTG TTC GTC GGT ACG CTC GAC CGC AAG TTA ATT GCG TTC GAT GAC ACC ACG GGC AAG 1560
 501 Leu Val Phe Val Gly Thr Leu Asp Arg Lys Leu Ile Ala Phe Asp Asp Thr Thr Gly Lys  520

1561 ATC CTG TGG ACC AGC CCG AAG CTC GAC AAC GCG ATC GAG TCC TTC CCG GTG ACC TTC ACG 1620
 521 Ile Leu Trp Thr Ser Pro Lys Leu Asp Asn Ala Ile Glu Ser Phe Pro Val Thr Phe Thr  540

1621 GCG GGC GAC AAG CAG TAC GTG GCC GTC GTC ACC AAT TGG TCG TCG GGC CTC GGC CGC CTG 1680
 541 Ala Gly Asp Lys Gln Tyr Val Ala Val Val Thr Asn Trp Ser Ser Gly Leu Gly Arg Leu  560

1681 AAG TCG ATC ACG CCG GAT GTG CAG CTT CCG CAG GAT AAC CCG CAT ACG GTG TAC GTC TTC 1740
 561 Lys Ser Ile Thr Pro Asp Val Gln Leu Pro Gln Asp Asn Pro His Thr Val Tyr Val Phe  580

1741 GCG CTG CCC GAC ACC AAG TAA 1761
 581 Ala Leu Pro Asp Thr Lys End  586
```

Fig 14

[SEQ ID No. 3]

```
1    ATG ACT ATC CGT CTC AAG ACC CTG CTG GCA TTC ACC GCG ATA ACC ACT CTC GCC CTG CCT    60
1    Met Thr Ile Arg Leu Lys Thr Leu Leu Ala Phe Thr Ala Ile Thr Thr Leu Ala Leu Pro    20

61   GCC TTC GCG CAG GAT GCG GCT GCC CCG GCC GCC CCG GCG GCG CGC ACC TAC AAG CCC GTG   120
21   Ala Phe Ala Gln Asp Ala Ala Ala Pro Ala Ala Pro Ala Ala Arg Thr Tyr Lys Pro Val    40

121  ACC AAC GAC ATG ATC CTC AAT CCG CCT GCC GAG GAA TGG ATC AGT TGG CGC CGC ACC GTC   180
41   Thr Asn Asp Met Ile Leu Asn Pro Pro Ala Glu Glu Trp Ile Ser Trp Arg Arg Thr Val    60

181  GAC AAC CAG GGC TAT AGT CCG CTC GAT CTC ATC AAC AAG GAT ATC GTC AAG AAC CTC GAG   240
61   Asp Asn Gln Gly Tyr Ser Pro Leu Asp Leu Ile Asn Lys Asp Ile Val Lys Asn Leu Glu    80

241  CTC GCC TGG GCC TGG CCG ATG GCC GCC GAC GGC CAG CAG GAG GCC GCT CCG CTC GTC CAT   300
81   Leu Ala Trp Ala Trp Pro Met Ala Ala Asp Gly Gln Gln Glu Ala Ala Pro Leu Val His   100

301  GAC GGC ATC ATG TTC CTG TCG ACC AAC CAG AAC ATC ATC CAG GCG CTC GAC GCC AAG ACC   360
101  Asp Gly Ile Met Phe Leu Ser Thr Asn Gln Asn Ile Ile Gln Ala Leu Asp Ala Lys Thr   120

361  GGC GAC CTC ATC TGG GAA TAC CGG CAC GTC CTG CCC GAA TTG CCC ACC TCC TGG GGC TAC   420
121  Gly Asp Leu Ile Trp Glu Tyr Arg His Val Leu Pro Glu Leu Pro Thr Ser Trp Gly Tyr   140

421  CAG CTC AAC CAG GCC CGT CGG CAG AAG AAC TCC ATC GCC CTC TAC GAC GAC AAG GTG ATC   480
141  Gln Leu Asn Gln Ala Arg Arg Gln Lys Asn Ser Ile Ala Leu Tyr Asp Asp Lys Val Ile   160

481  GTG GCC ACC GCC GAC GCC AAG CTG GTG GCG CTC GAT GCG GCC ACC GGC AAG GTC GCC TGG   540
161  Val Ala Thr Ala Asp Ala Lys Leu Val Ala Leu Asp Ala Ala Thr Gly Lys Val Ala Trp   180

541  GAA ACG CAG GTC TAT GAC ACC CAG AAG GGC TAC AGC TAT ACC GTC GGC CCG CTG ATC GTG   600
181  Glu Thr Gln Val Tyr Asp Thr Gln Lys Gly Tyr Ser Tyr Thr Val Gly Pro Leu Ile Val   200

601  AAC GAC AAG GTC ATC TCG GCC ATT TCC GGC TGC TCG ATC GCC GGC ACG GCG GGC GGC TGC   660
201  Gly Asp Thr Ala Val Tyr Gly Pro Ala Gly Gly Glu Tyr Gly Ile Arg Gly Trp Leu Glu   220

661  TTC ATC GCT GCG CAC GAT GCC AAG ACC GGC AAG GAA ATC TGG CGC TTC AAC ACC ATC GAT   720
221  Phe Ile Ala Ala His Asp Ala Lys Thr Gly Lys Glu Ile Trp Arg Phe Asn Thr Ile Asp   240

721  GAT CCC AAG AAC CCC GAG CAG GAA GCC TCC TGG AAC GGC GTC CCG CCG GAA AAC CGC TGG   780
241  Asp Pro Lys Asn Pro Glu Gln Glu Ala Ser Trp Asn Gly Val Pro Pro Glu Asn Arg Trp   260

781  GGC GGC ACG CCC TGG ACC ACG GGC TCC TAT GAT CCG CGC ACC AAT ACC ACC TTC TGG GGC   840
261  Gly Gly Thr Pro Trp Thr Thr Gly Ser Tyr Asp Pro Arg Thr Asn Thr Thr Phe Trp Gly   280

841  GTG GGC ATG CCC GGC CCC TAT TCC CAG CTC ATC CGC GGC TCG GGC GAG GGG CCG GTG CTC   900
281  Val Gly Met Pro Gly Pro Tyr Ser Gln Leu Ile Arg Gly Ser Gly Glu Gly Pro Val Leu   300
```

Fig. 15

[SEQ ID No.3] (be continued)

```
901  TAT ACC AAC AAC ACT CTG GCG CTC GAC GCC GAT ACC GGC GAG CGC AAG TGG AAC TTC TCG  960
301  Tyr Thr Asn Asn Thr Leu Ala Leu Asp Ala Asp Thr Gly Glu Arg Lys Trp Asn Phe Ser  320

961  CAC CTG CCC GCC GAT AAC TGG GAC CTG GAC AGC CCG TTC GAG CGC ATC CTC GTC GAT GAG  1020
321  His Leu Pro Ala Asp Asn Trp Asp Leu Asp Ser Pro Phe Glu Arg Ile Leu Val Asp Glu  340

1021 GGC CAG GGT GAC GCC GCC AAG CAC CTG CTC GTG ACG GTA CCC GGC AAG GAC GGC ATC GCC  1080
341  Gly Gln Gly Asp Ala Ala Lys His Leu Leu Val Thr Val Pro Gly Lys Asp Gly Ile Ala  360

1081 TTC GGG CTC GAT CGT GAT ACC GGC AAA TAT CTC TGG TCG CGC GAC ACG GTC TAT CAG AAC  1140
361  Phe Gly Leu Asp Arg Asp Thr Gly Lys Tyr Leu Trp Ser Arg Asp Thr Val Tyr Gln Asn  380

1141 GTC GTC AAG AAC ATC GAT GCC GAA GGC AAG GTG ACG CTC AAC AGC GAT CTG GTG CCT ACC  1200
381  Val Val Lys Asn Ile Asp Ala Glu Gly Lys Val Thr Leu Asn Ser Asp Leu Val Pro Thr  400

1201 GCG GTC AAC CAG GAG GTC TTC GTC TGC ACC TCG GTT TCG GGC GGC AAG CTC TGG ATG ACC  1260
401  Ala Val Asn Gln Glu Val Phe Val Cys Thr Ser Val Ser Gly Gly Lys Leu Trp Met Thr  420

1261 GGC GCC TAT AGC CCC AAG ACG CAG ACC TAT TAC GTG CCG CTG GCC GAG GCC TGC AAC ACC  1320
421  Gly Ala Tyr Ser Pro Lys Thr Gln Thr Tyr Tyr Val Pro Leu Ala Glu Ala Cys Asn Thr  440

1321 GTG ACC CCG ACC GTC ACC GAG TTC ACC GCC GGT AAC GCC GTG GGC GCC ACC AAG TTC GGG  1380
441  Val Thr Pro Thr Val Thr Glu Phe Thr Ala Gly Asn Ala Val Gly Ala Thr Lys Phe Gly  460

1381 CCG CGC GTG CTG CCG CCC AAC ATC ACC AAT GGC GGC GTG GTC GAA GCC ATC AAC GTT GCC  1440
461  Pro Arg Val Leu Pro Pro Asn Ile Thr Asn Gly Gly Val Val Glu Ala Ile Asn Val Ala  480

1441 GAT GGC GCC CGC AAG TGG CGG CTC GAA CAG CGC CCG ACC TTC AGC TCC TCG CTG CTG GCG  1500
481  Asp Gly Ala Arg Lys Trp Arg Leu Glu Gln Arg Pro Thr Phe Ser Ser Ser Leu Leu Ala  500

1501 ACC GCT GGC GGC CTG GTC TTC GGC GGC GAT GCC GGA CGC TTC CTC ATG GCC ATC GAC GAC  1560
501  Lys Ala Lys Val Leu Val Pro Arg Arg Leu Asn Gly Met Leu Ala Thr Gly Gly Asp Leu  520

1561 GAG ACC GGC CAG GTG GTG TGG AAG ACC CGC CTC AAC GCT CCG ATC GGC GGC TAT CCG ATG  1620
521  Glu Thr Gly Gln Val Val Trp Lys Thr Arg Leu Asn Ala Pro Ile Gly Gly Tyr Pro Met  540

1621 ACC TAT GAA ATC GAC GGC GAG CAA TAT CTG GCT GTA CCG ACC GGC TTC TCG GCC CAG GCC  1680
541  Thr Tyr Glu Ile Asp Gly Glu Gln Tyr Leu Ala Val Pro Thr Gly Phe Ser Ala Gln Ala  560

1681 AGC AGC TCC GCC TCG ATG TTC CCG GAA ATC CCG GTG CCC TCG GGC TCG GGC AAT TCG CTC  1740
561  Ser Ser Ser Ala Ser Met Phe Pro Glu Ile Pro Val Pro Ser Gly Ser Gly Asn Ser Leu  580

1741 TTC GTC TTC AAG CTG CGC AAC GAT ACC CAG ACC GCC AGC AAA TAG  1785
581  Phe Val Phe Lys Leu Arg Asn Asp Thr Gln Thr Ala Ser Lys End  594
```

Fig. 16

[SEQ ID No. 4]
GGCGAATGCATGTCCATAACTG

[SEQ ID No. 5]
CGGAAGACTGGGAATTCCG

[SEQ ID No. 6]
CACGTTGACACGCGTTCGTA

[SEQ ID No. 7]
GCATCAATACCGGGAGCAGG

[SEQ ID No. 8]
GGCCAAAACCCTTTGGGAGACCCCTGATG

[SEQ ID No. 9]
GTTCCGCGGCAGACGGAATCTTGCGTC

SEQUENCE LISTING

<160> NUMBER OF SEQ ID NOS: 15

<210> SEQ ID NO 1
<211> LENGTH: 599
<212> TYPE: PRT

<213> ORGANISM: Pseudogluconobacter

<400> SEQUENCE: 1

```
Met Leu Lys Gln Ser Leu Leu Ala Ser Gly Leu Ala Ala Leu Cys Val
1               5                   10                  15

Ala Ala Met Gly Ser Leu Ser Leu Ala Ala Glu Thr Thr Ser Glu Arg
            20                  25                  30

Leu Leu Asn Ala Gly Ser Glu Ala Glu Asn Gly Asn Trp Leu Met Val
        35                  40                  45

His Arg Thr Tyr Asp Ser His Arg Phe Ser Pro Leu Ser Glu Ile Asn
    50                  55                  60

Lys Asp Thr Ile Lys Asp Leu Gly Leu Ala Ser Val Thr Ile Leu Asp
65                  70                  75                  80

Asn Ala Ser Arg Gly Gly Arg Tyr Ala Ser Ala Arg Asn Glu Gly Thr
                85                  90                  95

Pro Leu Val Glu Asp Gly Phe Met Tyr Leu Gln Ser Gly Trp Ser Val
            100                 105                 110

Val Tyr Lys Leu Asp Val Arg Asp Gly Lys Thr Ala Lys Val Val Trp
        115                 120                 125

Lys Tyr Asp Pro Glu Val Asp Arg Gln Trp Val Ser Asp Ala Thr Cys
130                 135                 140

Cys Gly Ala Glu Asn Arg Gly Ile Gly Leu Trp Asn Asp Asp Val Val
145                 150                 155                 160

Ala Leu Thr Met Asp Gly Arg Val Met Ser Ile Asn Lys Asp Thr Gly
                165                 170                 175

Glu Leu Asn Trp Glu Lys Gln Arg Ala Asp Lys Ala Arg Ala Glu Ser
            180                 185                 190

Phe Thr Gly Ala Pro Leu Ile Ile Gly Asp Thr Ala Val Tyr Gly Pro
        195                 200                 205

Ala Gly Gly Glu Tyr Gly Ile Arg Gly Trp Leu Glu Ala Ile Asp Leu
    210                 215                 220

Lys Thr Gly Asp Val Ala Trp Arg Thr Tyr Thr Val Pro Gly Pro Gly
225                 230                 235                 240

Glu Pro Gly Asn Asp Thr Trp Gln Gly Asn Ala Trp Glu Thr Gly Gly
                245                 250                 255

Ala Ser Ile Trp Gln Thr Gly Ser Tyr Asp Pro Asp Thr Gly Met Thr
            260                 265                 270

Tyr Trp Gly Thr Gly Asn Pro Ala Pro Gln Ile Asp Ala Glu Tyr Arg
        275                 280                 285

Pro Gly Asp Asn Leu Tyr Ala Ser Ser Leu Leu Ala Leu Asp Ala Lys
    290                 295                 300

Asp Gly Ala Leu Lys Trp His Phe Gln Phe Thr Pro Asn Asp Pro Tyr
305                 310                 315                 320

Asp Tyr Asp Glu Ile Gly Asp Asn Gln Leu Leu Asp Val Ser Val Asp
                325                 330                 335

Gly Lys Pro Ser Lys Met Val Val Arg Ala Ala Arg Asn Gly Phe Met
            340                 345                 350

Tyr Gly Phe Asn Arg Leu Asp Gly Ala Met Thr Tyr Ala Lys Gln Tyr
        355                 360                 365

Val Glu Asp Leu Thr Trp Thr Thr Gly Ile Asp Pro Lys Thr Gly Lys
    370                 375                 380

Pro Leu Glu Tyr Asp Pro Lys Ala Gln Leu Gln Lys Tyr Val Ala Gly
385                 390                 395                 400
```

```
Thr Val Gly Ser Arg Glu Gly Asn Pro Gly Ile Tyr Cys Pro Thr Leu
            405                 410                 415

Gly Gly Gly Lys Asn Trp Gln Pro Ala Ala Tyr Ser Pro Asn Thr Lys
            420                 425                 430

Leu Leu Tyr Val Thr Ser Ala Glu Gly Cys Ser Ala Tyr Val Pro Glu
            435                 440                 445

Ala Ala Pro Asn Pro Thr Thr Thr Gly Gly Glu Tyr Asp Val Val Lys
450                 455                 460

Ala Gln Arg Glu Trp Asn Gly Arg Leu Pro Ala Pro Glu Gly Thr Lys
465                 470                 475                 480

Leu Pro Asp Val Phe Asn Gly Gly Ser Val Lys Ala Ile Asp Pro Leu
            485                 490                 495

Thr Gly Glu Thr Lys Ala Lys Val Leu Val Pro Arg Arg Leu Asn Gly
            500                 505                 510

Met Leu Ala Thr Gly Gly Asp Leu Val Trp Ser Ser Gly Thr Asp Gly
            515                 520                 525

Asn Leu Tyr Ala Tyr Asp Ala Asn Thr Leu Glu Thr Val Trp Thr Phe
            530                 535                 540

Asn Val Gly Thr Ala Leu Gly Gly Pro Pro Met Ser Tyr Ser Val Asp
545                 550                 555                 560

Gly Lys Gln Tyr Val Ala Val Leu Ala Gly Ala Ala Ser Ala Ala
            565                 570                 575

Asp Lys Lys Val Ala Pro Gln Ser Glu Phe Phe Val Pro Ala Asp Ala
            580                 585                 590

Leu Tyr Ile Phe Ala Leu Lys
            595

<210> SEQ ID NO 2
<211> LENGTH: 586
<212> TYPE: PRT
<213> ORGANISM: Pseudogluconobacter

<400> SEQUENCE: 2

Met Tyr Arg Lys Gly Ser Val Leu Thr Val Ser Ala Leu Val Leu Gly
1               5                   10                  15

Leu Cys Thr Ser Ser Val Trp Ala Gln Gln Ala Pro Thr Thr Asn Ala
                20                  25                  30

Leu Asp Asn Leu Thr Pro Val Thr Ser Val Trp Ala Gln Gln Ala Pro
            35                  40                  45

Thr Thr Asn Ala Leu Asp Asn Leu Thr Pro Val Thr Gly Trp Gly Tyr
        50                  55                  60

Ser Pro Leu Asp Gln Ile Asn Lys Asp Asn Val Asp Lys Leu Gln Leu
65                  70                  75                  80

Val Trp Ser Trp Gly Leu Ser Pro Gly Gly Thr Thr Gln Glu Thr Pro
                85                  90                  95

Leu Val His Asp Gly Val Met Phe Val Gln Asn Ser Ser His Leu Ile
            100                 105                 110

Gln Ala Leu Asp Ala Gly Thr Gly Glu Leu Leu Trp Gln Tyr Gln Tyr
            115                 120                 125

Ser Leu Pro Thr Gly Val Asn Pro Ala Gly Gln Arg Ser Lys Ala Leu
        130                 135                 140

Tyr Gly Asp Asn Leu Ile Phe Ala Thr Arg Asp Ala His Ile Val Ala
145                 150                 155                 160

Val Asn Ala Lys Thr Gly Lys Leu Ala Trp Asp Gln Gln Val Ala Asp
                165                 170                 175
```

```
Tyr Lys Lys Gly Trp Gly Tyr Ser Ser Gly Pro Leu Val Ala Asp Gly
            180                 185                 190

Thr Ile Ile Gln Gly Met Thr Asn Cys Gly Asn Gly Glu Pro Gly Gly
            195                 200                 205

Cys Phe Ile Thr Gly His Asp Pro Ala Thr Gly Lys Glu Leu Trp Arg
210                 215                 220

Leu Asn Thr Ile Ala Ser Gly Asp Thr Pro Glu Gly Asn Ser Trp Asn
225                 230                 235                 240

Gly Leu Pro Gln Met Ser Arg Tyr Gly Ala Ser Ala Trp Ile Thr Gly
                245                 250                 255

Ser Tyr Asp Pro Asp Gln Asn Ile Val Phe Ala Gly Val Gly Gln Pro
            260                 265                 270

Tyr Pro Trp Pro Ala Val Leu Asn Gly Leu Leu Pro Lys Ser Thr Asp
            275                 280                 285

Ser Lys Tyr Thr Asn Asn Ala Ala Tyr Thr Asp Ser Thr Leu Ala Ile
            290                 295                 300

Glu Pro Lys Thr Gly Ala Leu Lys Trp Tyr His Gln Tyr Leu Ala Thr
305                 310                 315                 320

Asp Thr Leu Asp Leu Asp Tyr Val Tyr Glu Arg Leu Leu Val Asp Leu
                325                 330                 335

Pro Val Lys Gly Glu Ala Thr Lys Gln Val Ile Thr Ala Gly Lys Leu
            340                 345                 350

Ala Ile Ile Glu Ser Leu Asp Arg Thr Ser Gly Lys Trp Leu Trp Ala
            355                 360                 365

His Glu Thr Val Pro Gln Asn Val Ser Ala Ile Asp Pro Val Thr
            370                 375                 380

Gly Glu Lys Thr Ile Asn Pro Asp Val Ile Pro Gln Val Gly Lys Thr
385                 390                 395                 400

Thr Val Asn Cys Pro Ala Asp Pro Gly Gly Arg Ala Trp Gln Ala Thr
                405                 410                 415

Ser Phe Ser Pro Lys Thr Gln Met Met Tyr Met Pro Thr Val Glu Phe
            420                 425                 430

Cys Ser Asn Thr Asp Val Asn Pro Leu Asp Pro Gly Asn Val Tyr Thr
            435                 440                 445

Gly Gly Gly Leu Ala Thr Phe Asn Arg Val Pro Arg Pro Asp Ser Asp
450                 455                 460

Gly Asn Ile Gly Gln Val Arg Ala Ile Asn Leu Ala Asp Gln Thr Asp
465                 470                 475                 480

Ala Trp Met Tyr Arg Gln His Ala Pro Val Thr Thr Ser Thr Leu Pro
                485                 490                 495

Thr Gly Gly Gly Leu Val Phe Val Gly Thr Leu Asp Arg Lys Leu Ile
            500                 505                 510

Ala Phe Asp Asp Thr Thr Gly Lys Ile Leu Trp Thr Ser Pro Lys Leu
            515                 520                 525

Asp Asn Ala Ile Glu Ser Phe Pro Val Thr Phe Thr Ala Gly Asp Lys
            530                 535                 540

Gln Tyr Val Ala Val Thr Asn Trp Ser Ser Gly Leu Gly Arg Leu
545                 550                 555                 560

Lys Ser Ile Thr Pro Asp Val Gln Leu Pro Gln Asp Asn Pro His Thr
                565                 570                 575

Val Tyr Val Phe Ala Leu Pro Asp Thr Lys
            580                 585
```

<210> SEQ ID NO 3
<211> LENGTH: 594
<212> TYPE: PRT
<213> ORGANISM: Pseudogluconobacter

<400> SEQUENCE: 3

```
Met Thr Ile Arg Leu Lys Thr Leu Leu Ala Phe Thr Ala Ile Thr Thr
1               5                   10                  15

Leu Ala Leu Pro Ala Phe Ala Gln Asp Ala Ala Pro Ala Ala Pro
            20                  25                  30

Ala Ala Arg Thr Tyr Lys Pro Val Thr Asn Asp Met Ile Leu Asn Pro
        35                  40                  45

Pro Ala Glu Glu Trp Ile Ser Trp Arg Arg Thr Val Asp Asn Gln Gly
    50                  55                  60

Tyr Ser Pro Leu Asp Leu Ile Asn Lys Asp Ile Val Lys Asn Leu Glu
65                  70                  75                  80

Leu Ala Trp Ala Trp Pro Met Ala Ala Asp Gly Gln Gln Glu Ala Ala
                85                  90                  95

Pro Leu Val His Asp Gly Ile Met Phe Leu Ser Thr Asn Gln Asn Ile
            100                 105                 110

Ile Gln Ala Leu Asp Ala Lys Thr Gly Asp Leu Ile Trp Glu Tyr Arg
        115                 120                 125

His Val Leu Pro Glu Leu Pro Thr Ser Trp Gly Tyr Gln Leu Asn Gln
    130                 135                 140

Ala Arg Arg Gln Lys Asn Ser Ile Ala Leu Tyr Asp Asp Lys Val Ile
145                 150                 155                 160

Val Ala Thr Ala Asp Ala Lys Leu Val Ala Leu Asp Ala Ala Thr Gly
                165                 170                 175

Lys Val Ala Trp Glu Thr Gln Val Tyr Asp Thr Gln Lys Gly Tyr Ser
            180                 185                 190

Tyr Thr Val Gly Pro Leu Ile Val Gly Asp Thr Ala Val Tyr Gly Pro
        195                 200                 205

Ala Gly Gly Glu Tyr Gly Ile Arg Gly Trp Leu Glu Phe Ile Ala Ala
    210                 215                 220

His Asp Ala Lys Thr Gly Lys Glu Ile Trp Arg Phe Asn Thr Ile Asp
225                 230                 235                 240

Asp Pro Lys Asn Pro Glu Gln Glu Ala Ser Trp Asn Gly Val Pro Pro
                245                 250                 255

Glu Asn Arg Trp Gly Gly Thr Pro Trp Thr Thr Gly Ser Tyr Asp Pro
            260                 265                 270

Arg Thr Asn Thr Thr Phe Trp Gly Val Gly Met Pro Gly Pro Tyr Ser
        275                 280                 285

Gln Leu Ile Arg Gly Ser Gly Glu Gly Pro Val Leu Tyr Thr Asn Asn
    290                 295                 300

Thr Leu Ala Leu Asp Ala Asp Thr Gly Glu Arg Lys Trp Asn Phe Ser
305                 310                 315                 320

His Leu Pro Ala Asp Asn Trp Asp Leu Asp Ser Pro Phe Glu Arg Ile
                325                 330                 335

Leu Val Asp Glu Gly Gln Gly Asp Ala Ala Lys His Leu Leu Val Thr
            340                 345                 350

Val Pro Gly Lys Asp Gly Ile Ala Phe Gly Leu Asp Arg Asp Thr Gly
        355                 360                 365

Lys Tyr Leu Trp Ser Arg Asp Thr Val Tyr Gln Asn Val Val Lys Asn
    370                 375                 380
```

```
Ile Asp Ala Glu Gly Lys Val Thr Leu Asn Ser Asp Leu Val Pro Thr
385                 390                 395                 400

Ala Val Asn Gln Glu Val Phe Val Cys Thr Ser Val Ser Gly Gly Lys
                405                 410                 415

Leu Trp Met Thr Gly Ala Tyr Ser Pro Lys Thr Gln Thr Tyr Tyr Val
            420                 425                 430

Pro Leu Ala Glu Ala Cys Asn Thr Val Thr Pro Thr Val Thr Glu Phe
                435                 440                 445

Thr Ala Gly Asn Ala Val Gly Ala Thr Lys Phe Gly Pro Arg Val Leu
        450                 455                 460

Pro Pro Asn Ile Thr Asn Gly Gly Val Val Glu Ala Ile Asn Val Ala
465                 470                 475                 480

Asp Gly Ala Arg Lys Trp Arg Leu Glu Gln Arg Pro Thr Phe Ser Ser
                485                 490                 495

Ser Leu Leu Ala Lys Ala Lys Val Leu Val Pro Arg Arg Leu Asn Gly
            500                 505                 510

Met Leu Ala Thr Gly Gly Asp Leu Glu Thr Gly Gln Val Val Trp Lys
        515                 520                 525

Thr Arg Leu Asn Ala Pro Ile Gly Gly Tyr Pro Met Thr Tyr Glu Ile
        530                 535                 540

Asp Gly Glu Gln Tyr Leu Ala Val Pro Thr Gly Phe Ser Ala Gln Ala
545                 550                 555                 560

Ser Ser Ser Ala Ser Met Phe Pro Glu Ile Pro Val Pro Ser Gly Ser
                565                 570                 575

Gly Asn Ser Leu Phe Val Phe Lys Leu Arg Asn Asp Thr Gln Thr Ala
            580                 585                 590

Ser Lys

<210> SEQ ID NO 4
<211> LENGTH: 10
<212> TYPE: PRT
<213> ORGANISM: Pseudogluconobacter

<400> SEQUENCE: 4

Ala Glu Thr Thr Ser Glu Arg Leu Leu Asn
1               5                   10

<210> SEQ ID NO 5
<211> LENGTH: 10
<212> TYPE: PRT
<213> ORGANISM: Pseudogluconobacter
<220> FEATURE:
<221> NAME/KEY: misc_feature
<222> LOCATION: (2)..(2)
<223> OTHER INFORMATION: Xaa can be any naturally occurring amino acid

<400> SEQUENCE: 5

Phe Xaa Ser Asn Thr Asp Val Asn Pro Leu
1               5                   10

<210> SEQ ID NO 6
<211> LENGTH: 10
<212> TYPE: PRT
<213> ORGANISM: Pseudogluconobacter

<400> SEQUENCE: 6

Ala Ser Trp Asn Gly Val Pro Pro Glu Asn
1               5                   10
```

<210> SEQ ID NO 7
<211> LENGTH: 1800
<212> TYPE: DNA
<213> ORGANISM: Pseudogluconobacter

<400> SEQUENCE: 7

```
atgctgaaac aaagcctgtt agcatcaggt ttagcggcgc tctgtgtcgc cgccatgggc      60
agcttgtcgc tggctgccga acgacgagc gagcgcctgc tcaatgccgg cagcgaggcc     120
gagaatggca actggctcat ggtgcaccgc acctatgaca gccatcgctt cagcccgctc     180
tccgagatca acaaggacac catcaaggac cttggcctgg cctccgtgac cattctggat     240
aatgcctcgc gcggcggccg ctatgccagc gcccgcaacg aaggcacgcc gctggtcgaa     300
gacggcttca tgtacctgca atccggctgg tccgtagtct ataagctcga cgtccgcgac     360
ggcaagaccg ccaaggtggt ctggaagtac gatccggaag tcgatcgcca gtgggtttcc     420
gacgccacct gctgcggcgc cgagaaccgc ggtatcggcc tgtggaacga cgacgtggtc     480
gccctgacca tggatggccg cgtcatgtcc atcaacaagg acaccggcga gctcaactgg     540
gaaaagcagc gcgctgacaa ggcgcgtgcc gaaagcttca ccggcgcccc gctcatcatc     600
ggcgacaccc ccgtttatgg tccggctggt ggcgaatacg gcatccgcgg ctggctcgaa     660
gccatcgacc tcaagaccgg cgatgtggcc tggcgtacct ataccgtgcc cggaccgggc     720
gagcccggca tgatacctg caggcaat gcctgggaaa ccggcggcgc ttccatctgg     780
cagacgggtt cctacgaccc cgataccggc atgacctatt ggggcacggg taacccggct     840
ccgcagatcg acgccgaata ccgtccggc gacaacctct atgcttcgag cctgctcgcg     900
ctcgacgcca aggatggtgc tctcaagtgg cacttccagt tcaccccgaa cgatccgtac     960
gactatgacg aaatcggcga caaccagctc ctggatgtga gcgtggatgg caagccgtcc    1020
aagatggtcg tccgcgctgc ccgtaacggt ttcatgtatg gcttcaaccg tctcgacggc    1080
gccatgacct atgccaagca gtatgtggaa gacctgacct ggaccaccgg catcgacccg    1140
aagaccggca gccgctcga atacgatccg aaggccagc tccagaagta cgtcgccggc    1200
accgttggct cgcgtgaagg caatccgggc atctactgcc cgacgctggg tggcggcaag    1260
aactggcagc tgctgcccta tagcccgaac accaagctcc tctacgtgac ctcggctgaa    1320
ggctgctcgg cctatgtgcc cgaggctgct cccaatccga cgaccaccgg cggtgaatac    1380
gacgtggtca aggctcagcg cgaatggaac ggccgtctgc cggctcctga aggcaccaag    1440
ctgccggacg tcttcaacgg cggctcggtc aaggccatcg acccgctcac cggcgaaacc    1500
aaggccaagg tcctggtgcc ccgccgcctg aacggcatgc tcgccaccgg tggcgacctg    1560
gtctggagct cgggcacgga tggtaacctc tatgcctatg acgccaacac tctggaaacc    1620
gtgtggacct tcaacgtcgg caccgcctt ggtggcccgc cgatgagcta ctcggtcgac    1680
ggcaagcagt acgtcgcggt tctcgccggt gctgccgcct ccgctgccga caagaaggtt    1740
gcgccgcagt ccgagttctt cgtgccggct gatgcgctct acatcttcgc gctgaagtaa    1800
```

<210> SEQ ID NO 8
<211> LENGTH: 1761
<212> TYPE: DNA
<213> ORGANISM: Pseudogluconobacter

<400> SEQUENCE: 8

```
atgtacagga aaggcagtgt gctgaccgtg tcagcactcg tcttggggct ttgcacatcg      60
tctgtgtggg cccagcaggc gccgacgacc aacgctctcg acaacctcac tcccgtcacc     120
```

```
gacgacgttc tcaagaaccc tgccgatggc gactggctga tggcccgccg aacttataac      180
ggctggggct acagcccct cgatcagatc aacaaggaca acgtcgacaa gcttcaactc       240
gtttggtcgt ggggtctgtc acccggcggc acgacgcagg agacgccgct cgttcatgat      300
ggcgtcatgt tcgttcagaa ttcgagccac ctcattcagg cgctcgatgc gggcactggc      360
gaactgctgt ggcagtacca gtattccctc cccaccggcg tcaatccggc cggccagcgc      420
tccaaggcgc tctatggtga caacctgatc tttgcgaccc gcgatgccca tatcgtcgcc      480
gtcaacgcca agaccggcaa gctggcctgg accagcagg tcgccgacta caagaagggc       540
tggggctatt cctcggggcc gctggtagcc gacggcacca tcatccaggg catgaccaat      600
tgcggcaacg gcgaacccgg cggctgcttc atcaccggcc acgacccagc gaccggtaag      660
gaattgtggc ggctcaacac catcgcgtcc ggcgacacgc ccgaaggcaa tagctggaac      720
ggcctgccgc agatgtcgcg ctatggcgct tcggcctgga tcaccggctc ctacgatccc      780
gaccagaaca tcgtcttcgc cggcgtcggc cagccgtatc cgtggccggc ggtgttgaac      840
gggcttctcc cgaagagcac ggattcgaag tacaccaaca atgcggctta taccgattcc      900
acgctggcga tcgagccgaa gaccggcgcg ctgaagtggt atcatcagta cctggccacc      960
gatacgctcg acctcgacta tgtgtatgag cgtctgctcg tcgatctgcc cgtcaagggc     1020
gaggcgacca agcaggtgat tactgccggc aagctcgcca tcatcgagtc gctcgaccgg     1080
acctcgggca gtggctctg gcgcacgaa acggtaccgc agaacgtggt gtcggccatc       1140
gatccggtca ccggcgagaa gaccatcaat cccgatgtga tcccgcaggt gggcaagacc     1200
acggtcaact gccctgccga cccgggcggc cgcgcctggc aggcgacttc gttcagcccg     1260
aagacgcaaa tgatgtatat gcccactgtc gagttctgct cgaataccga cgtcaacccg     1320
ctcgatccgg gccaggtcta taccggtggc ggtcttgcga ccttcaaccg cgtgccgcgg     1380
ccggatagcg atggcaatat cggtcaggtg cgcgccatca atcttgccga ccagacggat     1440
gcctggatgt atcgccagca cgctccggtc accacctcga cgctgccgac cggtggcggc     1500
ctggtgttcg tcggtacgct cgaccgcaag ttaattgcgt tcgatgacac cacgggcaag     1560
atcctgtgga ccagcccgaa gctcgacaac gcgatcgagt ccttcccggt gaccttcacg     1620
gcgggcgaca gcagtacgt ggccgtcgtc accaattggt cgtcgggcct cggccgcctg      1680
aagtcgatca cgccggatgt gcagcttccg caggataacc cgcatacggt gtacgtcttc     1740
gcgctgcccg acaccaagta a                                               1761
```

<210> SEQ ID NO 9  
<211> LENGTH: 1785  
<212> TYPE: DNA  
<213> ORGANISM: Pseudogluconobacter

<400> SEQUENCE: 9

```
atgactatcc gtctcaagac cctgctggca ttcaccgcga taaccactct cgccctgcct       60
gccttcgcgc aggatgcggc tgccccgcc gccccggcgg cgcgcaccta caagcccgtg       120
accaacgaca tgatcctcaa tccgcctgcc gaggaatgga tcagttggcg ccgcaccgtc      180
gacaaccagg gctatagtcc gctcgatctc atcaacaagg atatcgtcaa gaacctcgag      240
ctcgcctggg cctggccgat ggccgccgac ggccagcagg aggccgctcc gctcgtccat      300
gacggcatca tgttcctgtc gaccaaccag aacatcatcc aggcgctcga cgccaagacc      360
ggcgacctca tctgggaata ccggcacgtc ctgcccgaat gcccacctc ctggggctac       420
```

```
cagctcaacc aggcccgtcg gcagaagaac tccatcgccc tctacgacga caaggtgatc    480
gtggccaccg ccgacgccaa gctggtggcg ctcgatgcgg ccaccggcaa ggtcgcctgg    540
gaaacgcagg tctatgacac ccagaagggc tacagctata ccgtcggccc gctgatcgtg    600
aacgacaagg tcatctcggc catttccggc tgctcgatcg ccggcacggc gggcggctgc    660
ttcatcgctg cgcacgatgc caagaccggc aaggaaatct ggcgcttcaa caccatcgat    720
gatcccaaga accccgagca ggaagcctcc tggaacggcg tcccgccgga aaaccgctgg    780
ggcggcacgc cctggaccac gggctcctat gatccgcgca ccaataccac cttctggggc    840
gtgggcatgc ccggccccta ttcccagctc atccgcggct cgggcgaggg gccggtgctc    900
tataccaaca cactctggc gctcgacgcc gataccggcg agcgcaagtg gaacttctcg    960
cacctgcccg ccgataactg ggacctggac agcccgttcg agcgcatcct cgtcgatgag    1020
ggccagggtg acgccgccaa gcacctgctc gtgacggtac ccggcaagga cggcatcgcc    1080
ttcgggctcg atcgtgatac cggcaaatat ctctggtcgc gcgacacggt ctatcagaac    1140
gtcgtcaaga acatcgatgc cgaaggcaag gtgacgctca acagcgatct ggtgcctacc    1200
gcggtcaacc aggaggtctt cgtctgcacc tcggtttcgg gcggcaagct ctggatgacc    1260
ggcgcctata gccccaagac gcagacctat acgtgccgc tggccgaggc ctgcaacacc    1320
gtgaccccga ccgtcaccga gttcaccgcc ggtaacgccg tgggcgccac caagttcggg    1380
ccgcgcgtgc tgccgcccaa catcaccaat ggcggcgtgg tcgaagccat caacgttgcc    1440
gatggcgccc gcaagtggcg gctcgaacag cgcccgacct tcagctcctc gctgctggcg    1500
accgctggcg gcctggtctt cggcggcgat gccggacgct tcctcatggc catcgacgac    1560
gagaccggcc aggtggtgtg gaagacccgc ctcaacgctc cgatcggcgg ctatccgatg    1620
acctatgaaa tcgacggcga gcaatatctg gctgtaccga ccggcttctc ggcccaggcc    1680
agcagctccg cctcgatgtt cccggaaatc ccggtgccct cgggctcggg caattcgctc    1740
ttcgtcttca gctgcgcaa cgatacccag accgccagca aatag                    1785

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
ggcgaatgca tgtccataac tg                                              22

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
cggaagactg ggaattccg                                                  19

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
```

```
cacgttgaca cgcgttcgta                                                    20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
gcatcaatac cgggagcagg                                                    20

<210> SEQ ID NO 14
<211> LENGTH: 29
<212> TYPE: DNA
<213> ORGANISM: Artificial Sequence
<220> FEATURE:
<223> OTHER INFORMATION: Primer

<400> SEQUENCE: 14
ggccaaaacc ctttgggaga cccctgatg                                          29

<210> SEQ ID NO 15
<211> LENGTH: 27
<212> TYPE: DNA
<213> ORGANISM: Artificial Sequence
<220> FEATURE:
<223> OTHER INFORMATION: Primer

<400> SEQUENCE: 15
gttccgcggc agacggaatc ttgcgtc                                            27
```

D-GLUCARIC ACID PRODUCING BACTERIUM, AND METHOD FOR MANUFACTURING D-GLUCARIC ACID

TECHNICAL FIELD

The present invention relates to a microorganism having improved productivity of D-glucaric acid to be used for production of D-glucaric acid and a method for efficiently producing D-glucaric acid. More specifically, the present invention relates to a method for inexpensively and efficiently producing D-glucaric acid under reaction conditions in which the activities of two types of dehydrogenases, i.e. a specific pyrroloquinoline quinone-dependent alcohol dehydrogenase (PQQ-ADH (hereinafter this enzyme is designated as "1")) and a specific pyrroloquinoline quinone-dependent aldehyde dehydrogenase (PQQ-ALDH (hereinafter this enzyme is designated as "2")) are involved and the activities of a plurality of ALDHs (hereinafter the enzymes having similar properties are designed as "3") involved in production of keto acids are reduced or eliminated.

BACKGROUND ART

Known carboxylic acids derived from D-glucose typically include D-gluconic acid derivatized by oxidation of the aldehyde group of the D-glucose and D-glucuronic acid derivatized by oxidation of the hydroxymethyl group of the D-glucose. A dicarboxylic acid derivatized by oxidation of both aldehyde group and hydroxymethyl group thereof is referred to as D-glucaric acid which is contained naturally in fruit such as apples and grapefruit and vegetables of Brassicaceae such as broccoli and sprouts.

D-glucaric acid can strongly inhibit β-glucuronidase and thus can reduce the risk of development of cancer such as breast cancer, colon cancer, liver cancer, lung cancer and skin cancer (Non-Patent Reference 1). In the United States, D-glucaric acid is contained in dietary supplements in the form of calcium D-glucarate. D-glucaric acid is also used as a raw material for chelating agents, cement additives and the like. Moreover, in 2004, D-glucaric acid was identified by the U.S. Department of Energy as a building block chemical for the biorefinery (Non-Patent Reference 2), and thus is expected as a novel polymer material.

Various methods for preparation of D-glucaric acid have been previously reported including chemical synthesis methods, enzyme methods and fermentation methods. Many chemical synthesis methods utilize D-glucose as a starting material and there have been proposed a method in which nitric acid is used as an oxidizing agent (Patent Reference 1), a method in which platinum is used as an oxidation catalyst (Patent Reference 2) and a method in which 4-acetylamino-2,2,6,6-tetramethylpiperidin-1-oxyl is used as an oxidizing agent (Patent Reference 3).

Further, improved methods have also been previously disclosed in which the selectivity during oxidation reaction is increased and the yield of D-glucaric acid is significantly improved (Patent References 4 and 5). However these chemical synthesis methods are disadvantageous in that production cost is high because the methods require a high amount of chemicals and dedicated facilities and in that substances of environmental concern such as nitrogen oxides may often be produced secondarily.

Meanwhile enzyme methods and fermentation methods are advantageous because of milder reaction conditions and less damage to the environment than chemical synthesis methods. Enzyme methods reported include, for example, a method in which D-glucuronic acid is subjected to the action of a hexose oxidase, aldehyde dehydrogenase and aldehyde oxidase and converted to D-glucaric acid (Patent Reference 6) and a method in which D-glucuronic acid is subjected to the action of glucose oxidase (Patent Reference 7). However none of these methods has been put into practical use because of low reactivity of the enzymes.

Fermentation methods reported include, for example, a method in which myo-inositol-1-phosphate synthase gene derived from *Saccharomyces cerevisiae*, mouse myo-inositol oxygenase gene and uronic acid dehydrogenase gene derived from *Pseudomonas syringae* are introduced in *Escherichia coli* in order to convert D-glucose to D-glucaric acid (Patent Reference 8 and Non-Patent Reference 3). However, the maximum yield of glucaric acid is as low as 2.5 g/L which is a level industrially insufficient.

PATENT REFERENCES

Patent Reference 1: U.S. Pat. No. 2,436,659
Patent Reference 2: U.S. Pat. No. 2,472,168
Patent Reference 3: U.S. Pat. No. 6,498,269
Patent Reference 4: U.S. Pat. No. 5,599,977
Patent Reference 5: U.S. Pat. No. 7,692,041
Patent Reference 6: WO 02/074926
Patent Reference 7: Japanese Patent No. 3713530
Patent Reference 8: WO 2009/145838

NON-PATENT REFERENCES

Non-Patent Reference 1: Cancer Letters, 54, 1-8 (1990)
Non-Patent Reference 2: Top value added chemicals from biomass, Volume 1—Results of screening for potential candidates from sugars and synthesis gas. U.S. Department of Energy, Washington, D.C. Non-Patent Reference 3: Metab. Eng., 12(3), 298-305 (2010)

SUMMARY OF INVENTION

Subject to be Solved by Invention

Despite various production methods of D-glucaric acid that have been reported as described above, the technique that allows inexpensive production of D-glucaric acid in an industrial scale has not yet been established and thus the market price of D-glucaric acid is significantly higher than other oxidation products of D-glucose such as D-gluconic acid and D-glucuronic acid. Therefore the present inventors conducted intensive studies in order to establish a method for inexpensively and effectively producing D-glucaric acid using a microorganism having improved productivity of D-glucaric acid.

Specifically the present inventors, during the research and development, isolated and purified an alcohol dehydrogenase (ADH (1)) and aldehyde dehydrogenases (ALDH (2) and ALDH (3)) respectively from strains of *Pseudogluconobacter saccharoketogenes* having different productivity of D-glucaric acid, and studied the properties of the enzymes in detail.

As a result, the present inventors have found for the first time that, in order to efficiently produce D-glucaric acid, it is required that the activities of two types of dehydrogenases, a specific pyrroloquinoline quinone-dependent alcohol dehydrogenase (PQQ-ADH (1)) and a specific pyrroloquinoline quinone-dependent aldehyde dehydrogenase (PQQ-ALDH (2)) are present and the activities of a plurality of ALDH (3) enzymes involved in production of keto acids are reduced or eliminated. Thus the inventors have completed the present invention.

An object of the present invention is to provide a method for inexpensively and efficiently producing D-glucaric acid using a microorganism having improved productivity of D-glucaric acid and to provide the microorganism.

Means to Solve the Subject

The present invention that provides a solution to the above subject includes the following technical means:

(1) A microorganism characterized in that belongs to the genus *Pseudogluconobacter* and has all the following characteristics:

(A) having activity of a specific alcohol dehydrogenase ADH (1) involved in production of D-glucaric acid;

(B) having activity of a specific aldehyde dehydrogenase ALDH (2) involved in production of D-glucaric acid; and (C) having reduced or eliminated activity of aldehyde dehydrogenase ALDH (3) involved in production of keto acids.

(2) The microorganism according to (1) above, wherein the specific alcohol dehydrogenase ADH (1) comprises a pyrroloquinoline quinone-dependent enzyme having a molecular weight of 64,000±5,000 as measured by SDS-PAGE and a molecular weight of 120,000±10,000 as measured by gel filtration chromatography and has any of the following amino acid sequences (a) to (c):

(a) an amino acid sequence represented by SEQ ID NO: 1;

(b) an amino acid sequence derived from the amino acid sequence represented by SEQ ID NO: 1 by substitution, deletion, insertion and/or addition of one or more amino acids; and (c) an amino acid sequence having 80% or higher homology with the amino acid sequence represented by SEQ ID NO: 1.

(3) The microorganism according to (1) above, wherein the specific aldehyde dehydrogenase ALDH (2) comprises a pyrroloquinoline quinone-dependent enzyme having a molecular weight of 61,000±5,000 as measured by SDS-PAGE and a molecular weight of 180,000±10,000 as measured by gel filtration chromatography and has any of the following amino acid sequences (d) to (f):

(d) an amino acid sequence represented by SEQ ID NO: 2;

(e) an amino acid sequence derived from the amino acid sequence represented by SEQ ID NO: 2 by substitution, deletion, insertion and/or addition of one or more amino acids; and (f) an amino acid sequence having 80% or higher homology with the amino acid sequence represented by SEQ ID NO: 2.

(4) An alcohol dehydrogenase ADH (1) characterized in that comprises a pyrroloquinoline quinone-dependent enzyme having a molecular weight of 64,000±5,000 as measured by SDS-PAGE and a molecular weight of 120,000±10,000 as measured by gel filtration chromatography and has any of the following amino acid sequences (a) to (c):

(a) an amino acid sequence represented by SEQ ID NO: 1;

(b) an amino acid sequence derived from the amino acid sequence represented by SEQ ID NO: 1 by substitution, deletion, insertion and/or addition of one or more amino acids; and (c) an amino acid sequence having 80% or higher homology with the amino acid sequence represented by SEQ ID NO: 1.

(5) An aldehyde dehydrogenase ALDH (2) characterized in that comprises a pyrroloquinoline quinone-dependent enzyme having a molecular weight of 61,000±5,000 as measured by SOS-PAGE and a molecular weight of 180,000±10,000 as measured by gel filtration chromatography and has any of the following amino acid sequences (d) to (f):

(d) an amino acid sequence represented by SEQ ID NO: 2;

(e) an amino acid sequence derived from the amino acid sequence represented by SEQ ID NO: 2 by substitution, deletion, insertion and/or addition of one or more amino acids; and (f) an amino acid sequence having 80% or higher homology with the amino acid sequence represented by SEQ ID NO: 2.

(6) A method for producing D-glucaric acid or a salt thereof from one or more saccharides selected from the group consisting of D-glucose, D-gluconic acid and D-glucuronic acid characterized in that a reaction for producing the D-glucaric acid from the saccharides is catalyzed by the specific alcohol dehydrogenase according to (4) above and the specific aldehyde dehydrogenase ALDH according to (5) above.

(7) A method for producing D-glucaric acid or a salt thereof comprising producing D-glucaric acid by using the microorganism according to any one of (1) to (3) above or a processed product thereof in the presence of one or more saccharides selected from the group consisting of D-glucose, D-gluconic acid and D-glucuronic acid.

(8) A method for producing D-glucaric acid or a salt thereof comprising producing D-glucaric acid by using a genetically modified organism into which a gene of the alcohol dehydrogenase according to (2) above and a gene of the aldehyde dehydrogenase according to (3) above are introduced or a processed product of the organism in the presence of one or more saccharides selected from the group consisting of D-glucose, D-gluconic acid and D-glucuronic acid.

(9) The method for producing D-glucaric acid or a salt thereof according to (8) above, wherein the gene of the alcohol dehydrogenase has a base sequence of SEQ ID NO: 1 and the gene of the aldehyde dehydrogenase has a base sequence of SEQ ID NO: 2.

(10) The method for producing D-glucaric acid or a salt thereof according to (7) or (8) above, wherein the processed product is a cell homogenate, a cell extract or acetone powder.

(11) A method for producing D-glucaraldehyde comprising producing D-glucaraldehyde of intermediate A from D-glucose by using the microorganism according to (1) or (2) above or a processed product thereof or an enzyme thereof.

(12) A method for producing L-guluronic acid or a salt thereof comprising producing L-guluronic acid of intermediate B by using the microorganism according to any one of (1) to (3) above or a processed product thereof or the enzymes according to (4) and (5) above in the presence of one or both saccharides selected from D-glucose and D-gluconic acid.

The present invention is hereinafter further specifically illustrated.

The present invention provides (1) a microorganism belonging to the genus *Pseudogluconobacter* having improved productivity of D-glucaric acid because it has activities of PQQ-ADH (1) and PQQ-ALDH (2) involved in production of D-glucaric acid and has reduced or eliminated activity of ALDH (3) involved in production of keto acids, and (2) a method for producing D-glucaric acid or a salt thereof in which the reaction for producing D-glucaric acid from one or more saccharides selected from the group consisting of 0-glucose, D-gluconic acid and D-glucuronic acid is catalyzed by two enzymes, PQQ-ADH (1) and PQQ-ALDH (2), shown in FIG. 1.

The present invention further provides (3) a method for producing D-glucaric acid or a salt thereof by bringing one or more saccharides selected from the group consisting of 0-glucose, D-gluconic acid and D-glucuronic acid into contact with a cell having improved productivity of D-glucaric acid or a processed product thereof to produce D-glucaric acid, and (4) production methods of 0-glucaraldehyde and L-guluronic acid which are intermediates during production of D-glucaric acid.

The PQQ-ADH (1) according to the present invention has following features.

(1) Action:

It has ADH activity which oxidizes a hydroxymethyl group of 0-glucose and D-gluconic acid to give an aldehyde group in the presence of an electron acceptor such as 2,6-dichlorophenolindophenol, potassium ferricyanide, phenazine metasulphate and tetrazolium salts and ALDH activity that oxidizes the aldehyde group at the 6-position of D-glucaraldehyde (a dialdehyde of D-glucaric acid: intermediate A) to give a carboxyl group.

(2) Molecular Weight:

The molecular weight thereof is 64,000±5,000 as measured by SDS-PAGE and 120,000±10,000 as measured by gel filtration chromatography.

(3) Prosthetic Group:

It contains pyrroloquinoline quinone (PQQ) in the molecule thereof.

(4) Predicted Amino Acid Sequence:

It has the amino acid sequence represented by SEQ ID NO: 1. The predicted amino acid sequence includes a signal sequence.

ADHs produced by *Pseudogluconobacter saccharoketogenes* which have been known include alcohol dehydrogenase containing a rare earth element in the molecule (enzyme A, Japanese Patent No. 3056295) and PQQ-dependent alcohol/aldehyde dehydrogenase (enzyme B, Japanese Patent Application Laid-open No. 2003-159079).

The PQQ-ADH (1) according to the present invention is, similar to enzyme A, characterized by the feature in that the expression thereof is induced by addition of a rare earth element and has the same molecular weight as enzyme A. However there is no reference reporting that enzyme A has PQQ in the molecule and also has aldehyde dehydrogenation activity. The PQQ-ADH (1) according to the present invention has, similar to enzyme B, PQQ in the molecule and has aldehyde dehydrogenase activity. However, the PQQ-ADH (1) is different in molecular weight from enzyme B.

PQQ-ADH (1) has very low aldehyde dehydrogenase activity which oxidizes the aldehyde group at the 1-position of intermediate A to give L-guluronic acid (an uronic acid of L-gulose: intermediate B) and oxidizes the aldehyde group of intermediate B to give D-glucaric acid. However as the rate of these reactions is very low, it is difficult to produce D-glucaric acid from D-glucose or D-gluconic acid only by the action of PQQ-ADH (1).

The PQQ-ALDH (2) according to the present invention has following features.

(1) Action:

It has ALDH activity which oxidizes an aldehyde group of D-glucose, intermediate A, intermediate B and D-glucuronic acid to give a carboxyl group in the presence of an electron acceptor such as 2,6-dichlorophenolindophenol, potassium ferricyanide, phenazine metasulphate and tetrazolium salts.

(2) Molecular Weight:

The molecular weight thereof is 61,000±5,000 as measured by SDS-PAGE and 180,000±10,000 as measured by gel filtration chromatography.

(3) Prosthetic group:

It contains PQQ in the molecule thereof.

(4) Amino Acid Sequence:

It has the amino acid sequence represented by SEQ ID NO: 2.

PQQ-ALDH (2) does not catalyze the reactions for producing intermediate A and intermediate B respectively from D-glucose and D-gluconic acid, and thus PQQ-ALDH (2) alone cannot produce D-glucaric acid from D-glucose or D-gluconic acid. PQQ-ALDH (2) can oxidize D-glucuronic acid to give D-glucaric acid. However the rate of oxidation is low.

*Pseudogluconobacter saccharoketogenes* produces, in addition to PQQ-ALDH (2), multiple ALDH (3) enzymes that catalyze oxidation of aldehyde groups. Among the ALDH (3) enzymes, PQQ/Heme-ALDH (hereinafter this enzyme is designated as "4") having the highest activity has the following features.

(1) Action:

It mainly catalyzes the reactions in which, in the presence of an electron acceptor such as 2,6-dichlorophenolindophenol, potassium ferricyanide, phenazine metasulphate and tetrazolium salts, D-glucose or D-gluconic acid is oxidized to produce 2-keto-D-gluconic acid and D-glucuronic acid is oxidized to give D-glucaric acid.

(2) Molecular Weight:

The molecular weight thereof is 59,000±5,000 as measured by SDS-PAGE and 130,000±10,000 as measured by gel filtration chromatography.

(3) Prosthetic Group:

It contains PQQ and Heme c.

(4) Amino Acid Sequence:

It has the amino acid sequence represented by SEQ ID NO: 3.

Many ALDH (3) enzymes typically including PQQ/Heme-ALDH (4) produce byproducts, keto acids, when they are subjected to reaction with D-glucose or D-gluconic acid. Therefore in the strain used for production of D-glucaric acid, it is required to reduce or eliminate activities of the ALDH (3) enzymes.

Specific examples of a microorganism having improved productivity of D-glucaric acid that has PQQ-ADH (1) and PQQ-ALDH (2) activities and has reduced activities of a plurality of ALDH (3) enzymes include *Pseudogluconobacter saccharoketogenes* Rh47-3 strain (FERM BP-10820).

Rh47-3 strain is utilized for production of D-glucuronic acid (WO 2008/139844) and is a mutant strain of *Pseudogluconobacter saccharoketogenes* K591s strain (Japanese Patent Application Laid-open No. S 62-228288; FERM BP-1130) capable of oxidizing L-sorbose to give 2-keto-L-gulonic acid.

The reason that Rh47-3 and K591s strains are significantly different in productivity of D-glucaric acid is as follows: Rh47-3 strain has PQQ-ADH (1) and PQQ-ALDH (2) activities involved in production of D-glucaric acid and also has reduced activities of ALDH (3) enzymes that produce keto acids, and thus can efficiently produce D-glucaric acid from D-glucose, D-gluconic acid and D-glucuronic acid.

K591s strain has, on the other hand, PQQ-ADH (1) activity while having undetectable PQQ-ALDH (2) activity. Further, K591s strain has very strong activities of ALDH (3) enzymes (particularly PQQ/Heme-ALDH (4)). Therefore when K591s strain is subjected to reaction with D-glucose, D-gluconic acid or D-glucuronic acid, keto acids are mainly produced and consequently D-glucaric acid cannot be efficiently produced.

Examples of strains having similar characteristics as K591s strain include *Pseudogluconobacter saccharoketogenes* TH14-86 strain (FERM BP-1128), *Pseudogluconobacter saccharoketogenes* 12-5 strain (FERM BP-1129), *Pseudogluconobacter saccharoketogenes* 12-4 strain (FERM BP-1131), *Pseudogluconobacter saccharoketogenes* 12-15 strain (FERM BP-1132) and *Pseudogluconobacter saccharoketogenes* 22-3 strain (FERM BP-1133).

The strains mentioned above which have difficulty in production of D-glucaric acid have, however, PQQ-ALDH (2) gene. Therefore by mutating the strains so as to express PQQ-ALDH (2) activity and reduce or eliminate ALDH (3) enzymes activities, the modified strains suitable for production of D-glucaric acid can be obtained.

The mutation can be carried out by well-known methods without limitation. Examples of the methods include random mutagenesis by exposure to ultraviolet or radiation or chemical mutagenesis using N-methyl-N'-nitro-N-nitrosoguanidine or the like, and site specific mutagenesis by gene recombination. Alternatively Rh47-3 strain may be subjected to mutagenesis according to well-known methods in order to increase PQQ-ADH (1) and PQQ-ALDH (2) activities or eliminate ALDH (3) enzymes activities, thereby further increasing the productivity of D-glucaric acid.

It is also possible to prepare a recombinant to which PQQ-ADH (1) gene and PQQ-ALDH (2) gene have been introduced by gene manipulation and the recombinant is used for production of D-glucaric acid. In general DNA to be recombined is an autonomously replicating expression vector in which a target gene is incorporated. Therefore by obtaining DNA of PQQ-ADH (1) gene and PQQ-ALDH (2) gene according to the present invention, the DNA to be recombined can be relatively easily prepared according to well-known gene manipulation techniques.

The base sequences of PQQ-ADH (1) and PQQ-ALDH (2) genes are respectively represented by SEQ ID NOs: 1 and 2. An expression vector may be, but is not limited to, an autonomously replicating plasmid or the one that is integrated into the chromosome of a host cell after introduction thereof into the host cell and replicated with the chromosome, for example.

A host cell is not particularly limited as far as it is compatible with the expression vector in which the gene is incorporated and allows transformation of the vector. Various cells generally used in the art such as bacteria, yeast, fungi, animal cells and plant cells can be used. It is preferable that the host cell does not produce an enzyme acting on the substrate, i.e. D-glucose, D-gluconic acid or D-glucuronic acid.

A method for confirming the productivity of D-glucaric acid of cells obtained by mutagenesis or gene manipulation is not particularly limited and may be as follows, for example: cells cultivated under the same conditions are added to 1.0% (w/v) glucose solution containing 0.5% (w/v) calcium carbonate and the oxidation reaction is allowed to proceed while shaking. The produced D-glucaric acid may be quantified with a variety of analytical devices.

A nutrient medium used for cultivation of cells obtained by mutagenesis or gene manipulation may be either of a natural medium or a synthetic medium as far as it contains a carbon source, a nitrogen source, an inorganic substance and an optional micronutrient required by the cells used.

The nutrient medium may be any nutrient medium that can be utilized by cells. Examples of the carbon source include glucose, sucrose, lactose, starch and the like. Examples of the nitrogen source include inorganic nitrogen compounds such as ammonium sulphate, urea and sodium nitrate; and organic nitrogen compounds such as corn steep liquor, yeast extract and peptone. Examples of the inorganic substance include sodium salts, potassium salts, magnesium salts and iron salts which specifically include sodium chloride, dipotassium hydrogen phosphate, magnesium sulphate, ferrous sulphate and the like.

Optionally a rare earth element such as lanthanum chloride and cerium chloride may also be added. Particularly when bacteria of the genus *Pseudogluconobacter* are cultivated, addition of a rare earth element is required in order to induce PQQ-ADH (1) activity. Micronutrients and coenzymes such as pantothenic acid, biotin, thiamine and riboflavin may also be used appropriately.

A method for cultivation is preferably a shake culture method or an aeration stirring culture method both of which use a liquid medium. The temperature and pH during cultivation may be selected so as to be most suitable for growth of the cells used. For example, incase of bacteria of the genus of *Pseudogluconobacter*, the temperature range is 15 to 45° C., preferably 20 to 40° C. and more preferably 25 to 35° C. and the pH range is 4 to 9, preferably 5 to 8 and more preferably 6 to 7.

Cells may be cultivated until or longer than the time when cells start to show the growth and preferably cells are cultivated until PQQ-ADH (1) activity and PQQ-ALDH (2) activity exhibited by cells reaches maximum. The dissolved oxygen level during cultivation is not particularly limited. Generally the dissolved oxygen level is preferably 0.5 ppm or more, which can be obtained by adjusting the aeration or the stirring speed. Cultivation may be carried out by any system selected from batch culture, feeding culture and continuous culture.

Upon production of D-glucaric acid, cultured cells or a processed product thereof is added to the substrate, namely one or more carbohydrates selected from the group consisting of D-glucose, D-gluconic acid and D-glucuronic acid and oxidation reaction is carried out. D-glucuronic acid is oxidized by the action of PQQ-ALDH (2) to give D-glucaric acid; however D-glucuronic acid is not a particularly suitable starting material for production of D-glucaric acid because the above reaction rate is low and D-glucuronic acid is more expensive than D-glucose or D-gluconic acid. In case of production of intermediate A, the starting material used is D-glucose and in case of production of intermediate B, the starting material used is D-glucose and/or D-gluconic acid.

The "processed product" of cells includes a cell homogenate obtained by physical disruption of cells with a homogenizer or glass beads, a cell extract obtained by chemical treatment of cells with a surfactant or an enzyme and acetone powder of any of the foregoing. Cells or a processed product thereof can be immobilized on a carrier and then can be repeatedly used. Example of a method for immobilization include a method in which cells or a processed product thereof is adsorbed on a cellulose carrier, a ceramic carrier, a glass bead carrier and the like and a method in which cells or a processed product thereof is embedded in calcium alginate, carrageenan and the like.

The oxidation reaction is desirably carried out at the concentration of a substrate generally in the range of 0.1 to 10% (w/v) and preferably 1 to 5% (w/v). When the starting material is D-glucose, a low substrate concentration tends to generate D-glucaric acid via intermediate B and a high substrate concentration tends to generate D-glucuronic acid via intermediate A. Therefore when intermediate B or D-glucaric acid is produced, it is preferable to adjust the D-glucose concentration within the range of 1 to 2% (w/v), while when intermediate A is produced, it is preferable to adjust the D-glucose concentration within the range of 3 to 5% (w/v). The temperature is, similarly to the cultivation temperature, in the range of 15 to 45° C., preferably 20 to 40° C. and more preferably 25 to 35° C. pH is generally in the range of 4 to 9 and particularly preferably 5 to 8. In order to adjust pH, sodium hydroxide, potassium hydroxide, calcium carbonate or the like may be added.

In addition, it is desirable to use shaking or aeration stirring means during oxidation reaction. It is also preferable that the reaction is terminated at, when D-glucaric acid is produced, the whole amount of intermediate B in the reaction solution is oxidized, when intermediate A is produced, the whole amount of D-glucose is oxidized and when intermediate B is produced, the whole amount of intermediate A or D-gluconic acid is oxidized.

After the reaction, recovery of D-glucaric acid or a salt thereof from the reaction solution does not require a specific method in the present invention. Namely the recovery can be carried out by combining well known ion exchange resin, precipitation and crystallization methods. Similarly, recovery of intermediate A and intermediate B or a salt thereof does not require a specific method.

Advantageous Effects of Invention

The present invention may provide the following effects:
1) The present invention can provide a microorganism having increased productivity of D-glucaric acid.
2) The present invention allows inexpensive and effective production and provision of D-glucaric acid using a microorganism having increased productivity of D-glucaric acid.
3) The present invention can provide a microorganism belonging to the genus *Pseudogluconobacter* which has increased productivity of D-glucaric acid because it has activities of PQQ-ADH (1) and PQQ-ALDH (2) involved in production of D-glucaric acid and has reduced or eliminated activity of ALDH (3) involved in production of keto acids.
4) The present invention can provide a method for producing D-glucaric acid or a salt thereof from one or more carbohydrates selected from the group consisting of D-glucose, D-gluconic acid and D-glucuronic acid by the reaction catalyzed by two enzymes, PQQ-ADH (1) and PQQ-ALDH (2).
5) The present invention can provide a method for producing D-glucaric acid or a salt thereof by bringing the carbohydrate into contact with cells having increased productivity of D-glucaric acid or a processed product thereof.
6) The present invention can provide a method for producing D-glucaraldehyde (intermediate A) and L-guluronic acid (intermediate B) which are intermediates during production of D-glucaric acid.
7) The present invention can provide alcohol dehydrogenase ADH (1) having the amino acid sequence of SEQ ID NO: 1 or an amino acid sequence having 80% or higher homology therewith and aldehyde dehydrogenase ALDH (2) having the amino acid sequence of SEQ ID NO: 2 or an amino acid sequence having 80% or higher homology therewith.
8) The present invention can provide a transformant to which the production capability of D-glucaric acid has been conferred by introducing into a host cell one or both of a gene of alcohol dehydrogenase ADH (1) having the amino acid sequence of SEQ ID NO: 1 or an amino acid sequence having 80% or higher homology therewith and a gene of aldehyde dehydrogenase ALDH (2) having the amino acid sequence of SEQ ID NO: 2 or an amino acid sequence having 80% or higher homology therewith.
9) The present invention can provide a method for producing D-glucaric acid or a salt thereof from D-glucaraldehyde (intermediate A) and/or L-guluronic acid (intermediate B) by the action of PQQ-ALDH (2).

BRIEF DESCRIPTION OF THE DRAWINGS

FIG. 11 shows the base sequence and the amino acid sequence of SEQ ID NO: 1;

FIG. 12 is the continuation of SEQ ID NO: 1;

FIG. 13 shows the base sequence and the amino acid sequence of SEQ ID NO: 2;

FIG. 14 is the continuation of SEQ ID NO: 2;

FIG. 15 shows the base sequence and the amino acid sequence of SEQ ID NO: 3;

FIG. 16 is the continuation of SEQ ID NO: 3; and

FIG. 17 shows the base sequences of SEQ ID NOs: 4 to 9.

BEST MODE FOR CARRYING OUT THE INVENTION

Figure 1:
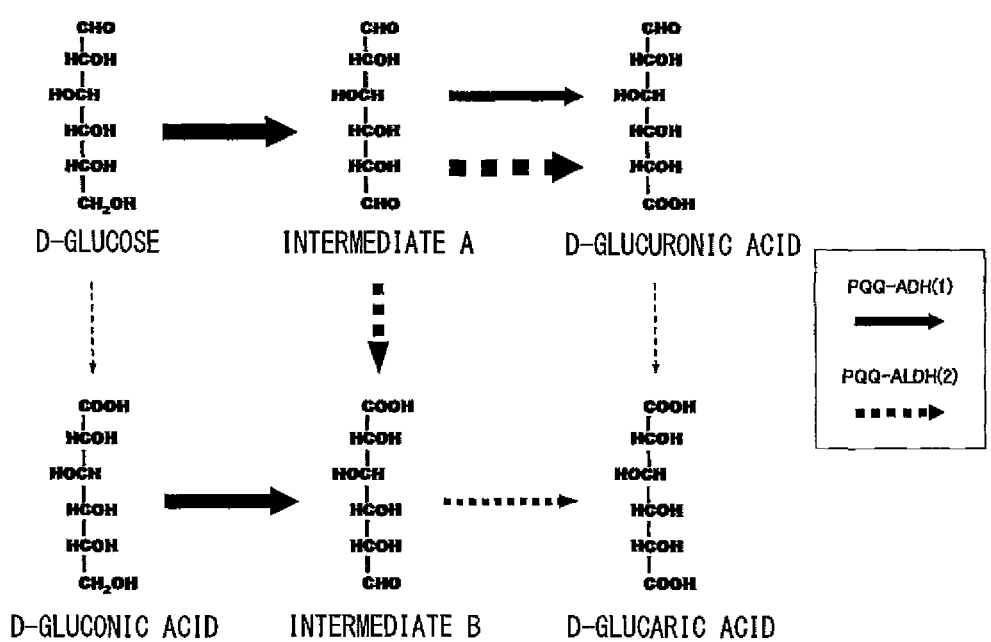
FIG. 1 is a figure showing reaction properties of PQQ-ADH (1) and PQQ-ALDH (2). An arrow having a larger size indicates a higher reactivity.

The present invention is hereinafter specifically described based on Examples which do not limit the present invention.

Example 1

In the present Example, the production ability of D-glucaric acid was compared between strains of *Pseudogluconobacter saccharoketogenes*.

(1) Cultivation of *Pseudogluconobacter Saccharoketogenes*

The strains used were *Pseudogluconobacter saccharoketogenes* Rh47-3 strain, *Pseudogluconobacter saccharoketogenes* TH14-86 strain, *Pseudogluconobacter saccharoketo-* genes 12-5 strain, *Pseudogluconobacter saccharoketogenes* K591s strain, *Pseudogluconobacter saccharoketogenes* 12-4 strain, *Pseudogluconobacter saccharoketogenes* 12-15 strain and *Pseudogluconobacter saccharoketogenes* 22-3 strain.

One platinum loop of each strain grown on an agar slant medium was inoculated in a test tube containing 10 mL of a preculture medium containing 1.0% of lactose, 1.0% of yeast extract, 2.0% of corn steep liquor and 0.3% ammonium sulphate (pH 7.0) and was subjected to the shake culture that carried out at 30° C. for 72 hours to prepare a preculture solution. The preculture solution (1 mL) was then inoculated into a Sakaguchi flask containing 100 mL of a main culture medium containing 2.0% of lactose, 0.5% of yeast extract, 1.0% of corn steep liquor, 0.5% of ammonium sulphate, 0.1% of ferrous sulphate and 0.01% of lanthanum chloride (pH 7.0) and was subjected to the shake culture that carried out at 30° C. for 72 hours.

(2) Measurement of ADH (1) Activity and ALDH (2 and 3) Activity

The ADH (1) activity and the ALDH (2 and 3) activity of the cultivated strains were measured as follows.

1) Measurement of Activity of ADH (1)

<Reagents>

Substrate solution: 0.2 M glucose solution

Buffer: McIlvaine buffer (pH 5.0)

Potassium ferricyanide solution: 0.1 M potassium ferricyanide solution

Reaction termination solution: 5 g of ferric sulphate and 95 mL of phosphoric acid were dissolved in pure water and adjusted to 1 L.

<Measurement Procedures>

The culture solution (1 mL) was centrifuged at 10,000 rpm for 5 minutes to recover the cells. The cells were resuspended in 1 mL of 0.9% saline. The cell suspension was appropriately diluted in 0.9% saline to obtain a crude enzyme solution. In a test tube 250 μL of the buffer, 500 μL of the substrate solution and 50 μL of the crude enzyme solution were placed and preliminarily heated to 30° C. for 5 minutes.

To the mixture 200 μL of the potassium ferricyanide solution was added to initiate oxidation reaction. After 10 minutes, 500 μL of the reaction termination solution was added to terminate the reaction. The reaction solution was added with 3.5 mL of pure water, left to stand in the dark at room temperature for 20 minutes and measured for the absorbance at 660 nm. For the control, pure water was used instead of the substrate solution. In this measurement, 1 U is defined as the amount of enzyme required to oxidize 1 μM of the substrate per minute.

2) Measurement of Activity of ALDH (2 and 3)

<Reagents>

Substrate solution: 0.2 M sodium glyoxylate solution (adjusted to pH 8.0 with sodium hydroxide)

Buffer: McIlvaine buffer (pH 8.0)

Other reagents and preparation methods thereof and measurement procedures are in accordance with the measurement of ADH (1) activity.

The results of measurement of enzyme activities of the strains are shown in Table 1. All strains had equivalent ADH (1) activity. Rh47-3 strain showed lower ALDH (2 and 3) activity than other strains.

TABLE 1

ADH (1) activity and ALDH (2 and 3) activity of strains

| Strain | ADH (1) activity (U/mL) | ALDH (2 and 3) activity (U/mL) |
| --- | --- | --- |
| Rh47-3 | 3.8 | 27.3 |
| TH14-86 | 4.1 | 278.8 |
| 12-5 | 4.3 | 170.0 |
| K591s | 3.6 | 286.6 |
| 12-4 | 4.0 | 118.6 |
| 12-15 | 4.3 | 115.0 |
| 22-3 | 3.7 | 143.3 |

(3) Production of D-Glucaric Acid

The culture solution (10 mL) was centrifuged at 10,000 rpm for 5 minutes to recover the cells. A substrate solution (10 mL; 60 mM D-glucose, 100 mM sodium D-gluconate, 50 mM sodium D-glucuronate) containing the equivalent amount of calcium carbonate was added to the cells of each strain and was subjected to the oxidation reaction that carried out at 30° C. for 60 hours while shaking. To the reaction solution (20 μL) 980 μL of 0.2 N hydrochloric acid was added to dissolve calcium carbonate followed by analysis for reaction products under the following conditions:

<Analysis of Reaction Products>

Instrument: carbohydrate analysis system ICS-3000, available from DIONEX

Analytical column: CarboPac PA-1 (inner diameter 4 mm×250 mm)

Detector: a pulsed amperometric detector

Eluent A: 100 mM sodium hydroxide

Eluent B: 100 mM sodium hydroxide containing 1 M sodium acetate

Analysis period: 12 minutes

Gradient condition: the concentration of eluent B was linearly increased from 0% to 100% over 12 minutes from the start of the analysis.

Column temperature: 35° C.

Flow rate: 1.0 mL/min

Standard substances used were D-glucose (Wako Pure Chemical Industries, Ltd.), D-gluconic acid sodium salt (Wako Pure Chemical Industries, Ltd.), D-glucuronic acid sodium salt monohydrate (Wako Pure Chemical Industries, Ltd.), 2-keto-D-gluconic acid hemicalcium salt (Wako Pure Chemical Industries, Ltd.) and D-glucaric acid monopotassium salt (SIGMA). Intermediate A and a sodium salt of intermediate B were prepared according to Examples 2 and 3.

The molar yield of each product after reaction with D-glucose is shown in Table 2 for Rh47-3 strain as well as other strains. The molar yield of each product after reaction with sodium D-gluconate and the molar yield of each product after reaction with sodium D-glucuronate are shown in Tables 3 and 4, respectively. With any of the substrates, Rh47-3 strain produced the highest amount of D-glucaric acid. Each strain other than Rh47-3 strain produced mainly 2-keto-D-gluconic acid after reaction with D-glucose or sodium D-gluconate and mainly two unknown substances after reaction with sodium D-glucuronate.

TABLE 2

Molar yield (%) of products after reaction with D-glucose

| Strain | D-glucuronic acid | D-glucaric acid | 2-keto-D-gluconic acid | Other substances |
|---|---|---|---|---|
| Rh47-3 | 25.6 | 50.3 | 1.3 | 22.8 |
| TH14-86 | 6.7 | 12.9 | 60.8 | 19.6 |
| 12-5 | 18.2 | 10.4 | 49.5 | 21.9 |
| K591s | 9.4 | 19.1 | 53.7 | 17.8 |
| 12-4 | 16.3 | 8.4 | 57.0 | 18.3 |
| 12-15 | 12.1 | 11.0 | 61.2 | 15.7 |
| 22-3 | 11.5 | 13.1 | 55.5 | 19.9 |

TABLE 3

Molar yield (%) of products after reaction with sodium D-gluconate

| Strain | Intermediate B | D-glucaric acid | 2-keto-D-gluconic acid | Other substances |
|---|---|---|---|---|
| Rh47-3 | 1.6 | 81.2 | 2.8 | 14.4 |
| TH14-86 | 0 | 9.7 | 61.3 | 29.0 |
| 12-5 | 0 | 22.3 | 53.7 | 24.0 |
| K591s | 0 | 27.2 | 47.3 | 25.5 |
| 12-4 | 0 | 6.4 | 65.9 | 27.7 |
| 12-15 | 0 | 22.1 | 51.6 | 26.3 |
| 22-3 | 0 | 16.2 | 55.3 | 28.5 |

TABLE 4

Molar yield (%) of products after reaction with sodium D-glucuronate

| Strain | D-glucuronic acid | D-glucaric acid | Other substances |
|---|---|---|---|
| Rh47-3 | 58.6 | 36.1 | 5.3 |
| TH14-86 | 32.1 | 12.4 | 55.5 |
| 12-5 | 41.2 | 16.5 | 42.3 |
| K591s | 20.8 | 21.3 | 57.9 |
| 12-4 | 42.5 | 18.8 | 38.7 |
| 12-15 | 39.3 | 11.7 | 49.0 |
| 22-3 | 37.7 | 10.9 | 51.4 |

Example 2

In the present Example, intermediate A was prepared during production of D-glucaric acid by *Pseudogluconobacter saccharoketogenes* and the structure of intermediate A was examined.

(1) Preparation of Intermediate A

To 500 mL of 5% (w/v) D-glucose solution, washed cells (from 500 mL of main culture) of *Pseudogluconobacter saccharoketogenes* Rh47-3 strain cultivated according to the method described above were added and was subjected to the oxidation reaction that initiated at 30° C., 150 rpm, aeration of 0.2 L/min.

The analysis of the sample was carried out over time while adjusting pH to 7.0 with 1M sodium hydroxide solution. When D-glucose of the sample was completely oxidized, the sample was centrifuged at 10,000 rpm for 10 minutes to collect a reaction solution (intermediate A: 17.8%, intermediate B: 2.8%, D-glucuronic acid: 75.2%, D-glucaric acid: 1.9% and other substances: 2.3%).

A portion of the collected reaction solution (solid matter: 5.0 g) was sequentially applied to a column containing 1 L of strong acid ion exchange resin PK-216 (Mitsubishi Chemical Corporation) and a column containing 3 L of weak base ion exchange resin IRA-96SB (Organo Corporation) in order to elute only intermediate A. The eluate was added with 1% (w/w) of active carbon to decolorize followed by freeze-drying to obtain 0.8 g powder of intermediate A with a purity of 98.0%.

(2) Examination of Structure of Intermediate a

A methanol solution of intermediate A was used for mass spectrometry under the following analytical conditions.

Instrument: FINNIGAN LCQ-DECA mass spectrometer available from Thermo Quest Corporation Ion source: ESI Spray voltage: 7 kV Capillary voltage: −11 V Capillary temperature: 150° C.

Sample concentration: 50 µg/mL

Sample introduction rate: 10 µL/min

Figure 2:
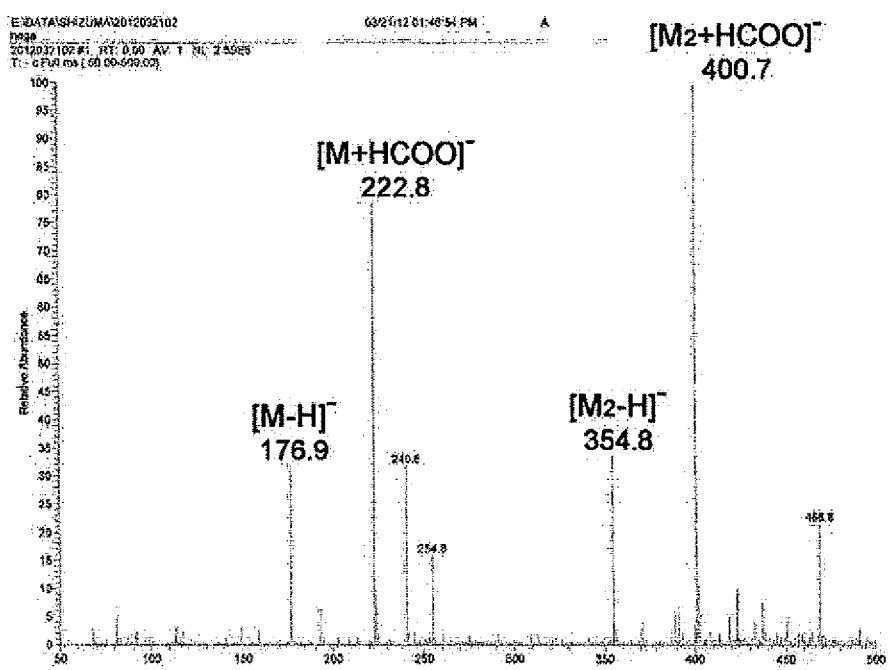
FIG. 2 is a diagram showing the result of mass spectrometry of intermediate A.

The result of mass spectrometry of intermediate A is shown in FIG. 2. As a result, negative ion peaks, $[M-H]^-$ 176.9 and $[M_2-H]^-$ 354.8, were detected. In the presence of formic acid, two negative ion peaks, $[M+HCOO]^-$ 222.8 and $[M_2+HCOO]^-$ 400.7, were detected. Based on the intensity of peaks, it was predicted that the complex with formic acid was produced more easily than negative ions produced by deprotonation and it was confirmed that the complex was not a dicarboxylic acid but a dialdehyde having a molecular mass of 178.

An aqueous solution of intermediate A sample was used for measurement of reducing ability by the Somogyi-Nelson method and also subjected to a measurement of total sugar amount by the phenol-sulphuric acid method. The results showed that the ratio of (amount of reducing sugar)/(amount of total sugar) was 8.02, confirming the strong reducing ability. From these results, it was predicted that intermediate A had a structure of D-glucaraldehyde which is a derivative of D-glucose having aldehyde groups at both C1 and C6 positions.

Example 3

In the present Example, intermediate B was prepared during production of D-glucaric acid by *Pseudogluconobacter saccharoketogenes* and the structure of intermediate B was examined.

(1) Preparation of Sodium Salt of Intermediate B

To 500 mL of 3% (w/v) sodium D-gluconate solution, centrifuged cells (from 500 mL of main culture) of *Pseudogluconobacter saccharoketogenes* Rh47-3 strain cultivated according to the method described above were added and was subjected to the oxidation reaction that initiated at 30° C., 150 rpm, aeration of 0.2 L/min. The analysis of the sample was carried out over time while adjusting pH to 7.0 with 1 M sodium hydroxide solution. When D-gluconic acid was completely oxidized, the sample was centrifuged at 10,000 rpm for 10 minutes to collect a reaction solution (intermediate B: 71.4%, D-glucaric acid: 26.0% and other substances: 2.6%).

A portion of the collected reaction solution (solid matter: 5.0 g) was concentrated to a solid matter of 70% followed by cooling to 20° C. to crystallize the sodium salt of intermediate B. The crystal was washed with 30% (v/v) ethanol and then dried under reduced pressure at 30° C. for 3 hours to obtain 1.3 g of the sodium salt of intermediate B with a purity of 99.5%.

(2) Examination of Structure of Intermediate B

A methanol solution of intermediate B was used for mass spectrometry under the following analytical conditions.

Figure 3:
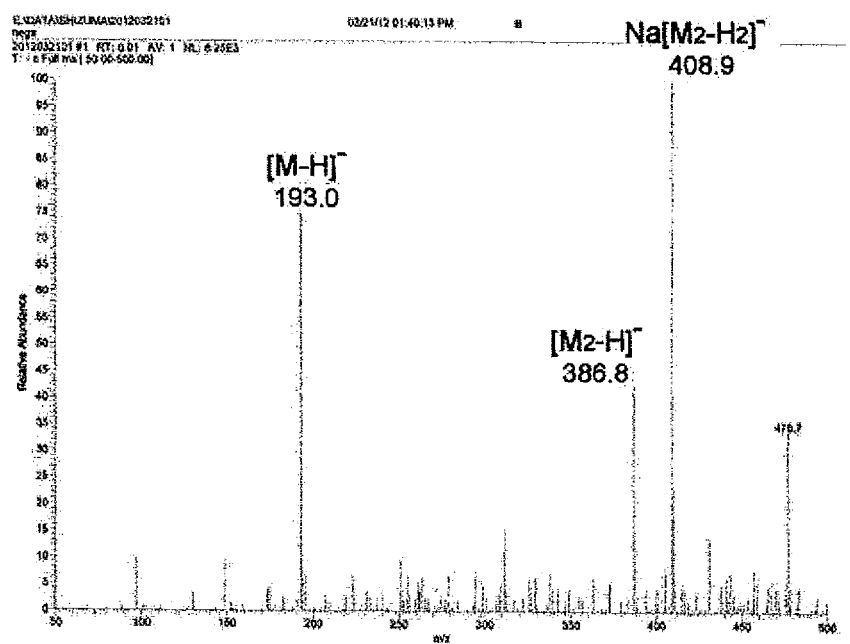
FIG. 3 is a diagram showing the result of mass spectrometry of intermediate B.
Figure 4:
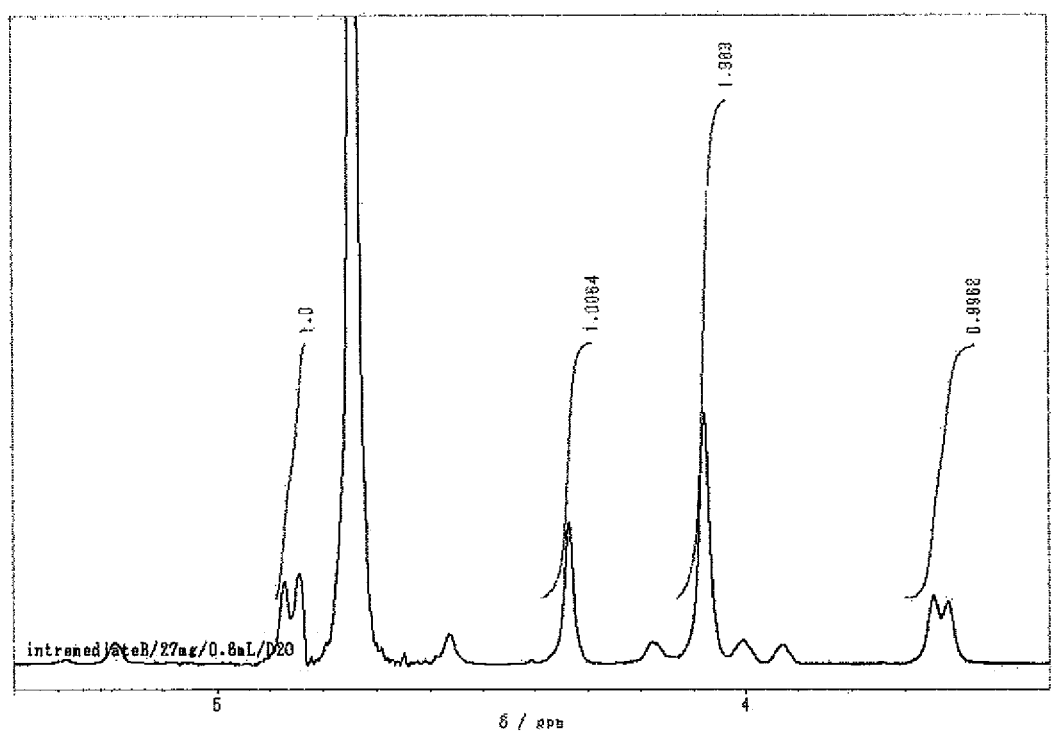
FIG. 4 is a diagram showing the result of $^{1}$H-NMR of intermediate B.
Figure 5:
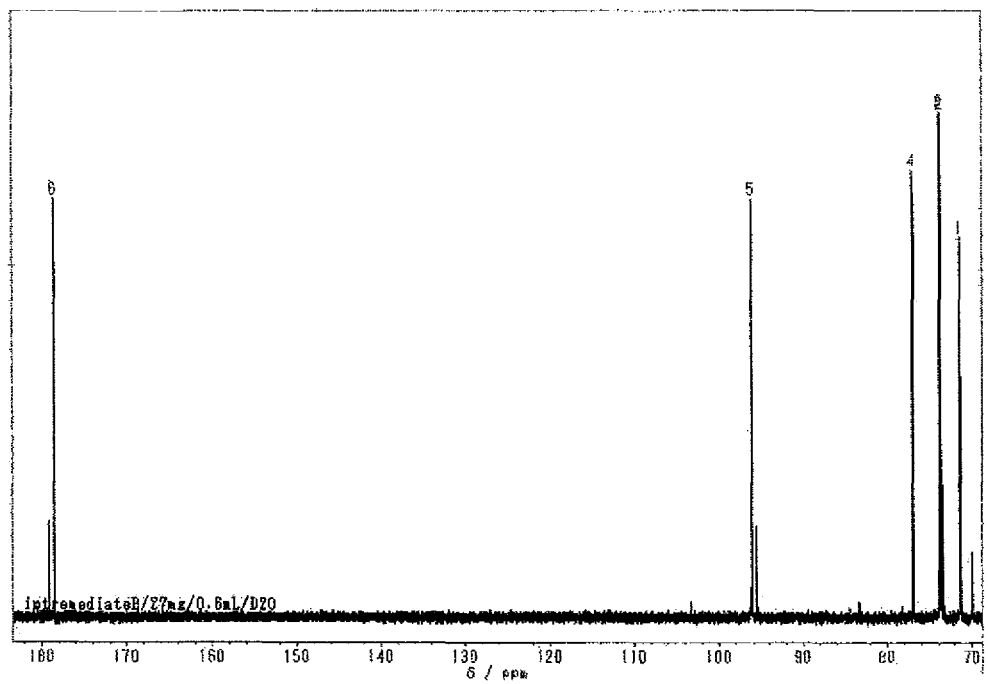
FIG. 5 is a diagram showing the result of $^{13}$C-NMR of intermediate B.
Figure 6:
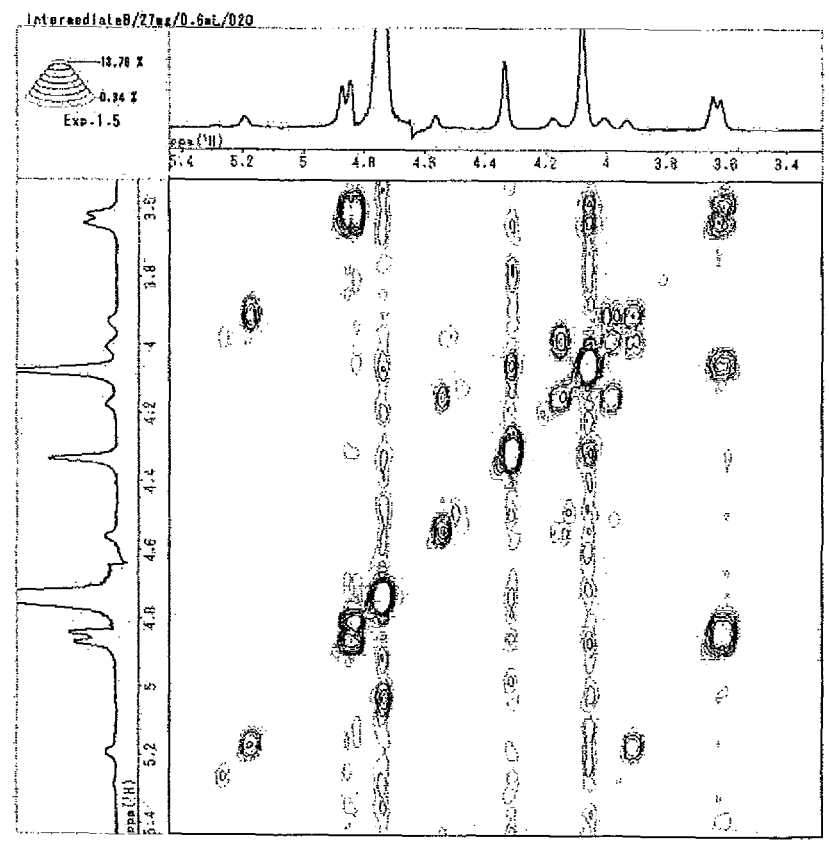
FIG. 6 a diagram showing the result of H,H-COSY NMR of intermediate B.
Figure 7:
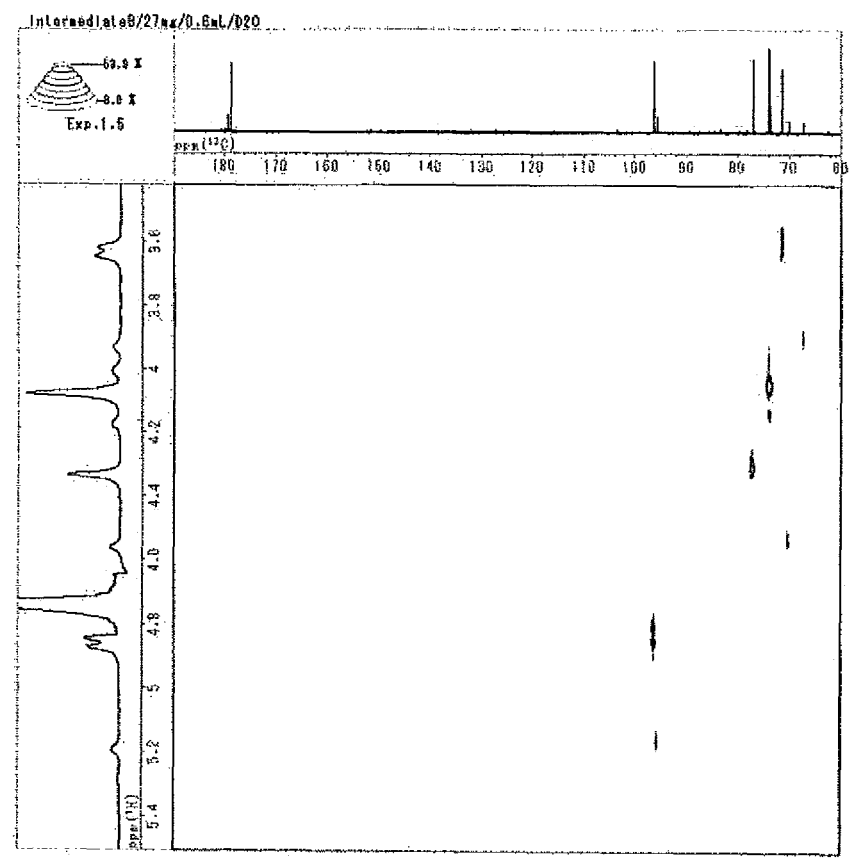
FIG. 7 a diagram showing the result of C,H-COSY NMR of intermediate B.

Instrument: FINNIGAN LCQ-DECA mass spectrometer available from Thermo Quest Corporation Ion source: ESI
Spray voltage: 5 kV
Capillary voltage: −11 V
Capillary temperature: 250° C.
Sample concentration: 50 μg/mL
Sample introduction rate: 10 μL/min The result of mass spectrometry of intermediate B is shown in FIG. 3.

As a result, negative ion peaks, $[M_2-H]^-$ 193.0 and $[M_2-H]^-$ 386.8 and $Na[M_2-H_2]^-$ 408.9 were detected. It was predicted that the molecular mass of intermediate B was 194.

FIGS. 4, 5, 6 and 7 respectively show the results of $^1$H-NMR (300 MHz, $D_2O$), $^{13}$C-NMR (75 MHz, $D_2O$), H,H-COSY (300 MHz, $D_2O$) and C,H-COSY (75 MHz, $D_2O$) of intermediate B.

According to the results of $^1$H-NMR and $^{13}$C-NMR, the spectra were assigned as follows: $^1$H-NMR (300 MHz, $D_2O$) δ 4.86 (d, 1H, $^3J_{1,2}$=8.6 Hz, H1), 4.33 (s, 1H, H5), 4.08 (s, 2H, H3 and H4), 3.63 (d, 1H, $^3J_{1,2}$=8.6 Hz, H1). $^{13}$C-NMR (75 MHz, $D_2O$) δ 178.6 (C6), 96.2 (C1), 77.1 (C5), 74.0 (C3 or C4), 73.8 (C4 or C3), 71.5 (C2).

From these results, intermediate B had a structure derived from D-glucose having a carboxyl group and an aldehyde group on each end that was different from the structure of D-glucuronic acid, and thus it was predicted that intermediate B was L-guluronic acid (uronic acid of L-gulose).

Example 4

In this Example, ADH (1), ALDH (2) and ALDH (3) were purified.

(1) Cultivation of *Pseudogluconobacter saccharoketogenes*

One platinum loop of each of *Pseudogluconobacter saccharoketogenes* Rh47-3 strain and *Pseudogluconobacter saccharoketogenes* K591s strain grown on an agar slant medium was inoculated in a test tube containing 10 mL of a seed culture medium containing 1.0% of lactose, 1.0% of yeast extract, 2.0% of corn steep liquor and 0.3% ammonium sulphate (pH 7.0) and was subjected to the shake culture that carried out at 30° C. for 72 hours.

Then 1 mL of each seed culture solution was inoculated into three Sakaguchi flasks respectively containing 100 mL of a preculture medium containing 1.0% of lactose, 1.0% of yeast extract, 2.0% of corn steep liquor and 0.3% of ammonium sulphate (pH 7.0) and was subjected to the shake culture that carried out at 30° C. for 72 hours.

Finally the whole amount of preculture solution was inoculated to a fermenter containing 30 L of a main culture medium containing 2.0% of lactose, 0.5% of yeast extract, 1.0% of corn steep liquor, 0.5% of ammonium sulphate, 0.1% of ferrous sulphate and 0.01% lanthanum chloride (pH 7.0) and was subjected to the main culture that carried out under the conditions of 30° C., aeration of 10 L/min, stirring of 250 rpm for 72 hours. The culture solution was centrifuged at 10,000 rpm for 10 minutes. The recovered cells were washed twice with 0.9% saline. Accordingly from the 30-L culture solution, about 90 g of wet cells of each strain were obtained.

(2) Preparation of Cell Extract Fraction

The recovered wet cells (30 g) were suspended in 100 mL of 10 mM phosphate buffer (pH 6.5) and disrupted on a French press. The solution obtained by disruption was centrifuged at 18,000 rpm for 15 minutes and the supernatant thereof was recovered. The obtained supernatant was further centrifuged at 30,000 rpm for 60 minutes and the supernatant thereof was recovered as a cell extract fraction.

(3) Ion Exchange Chromatography

Each cell extract fraction of Rh47-3 strain and K591s strain was applied to a column (inner diameter 5.6 cm×5 cm) containing TOYOPEARL DEAE-650M (Tosoh Corporation) which had been previously equilibrated with 10 mM phosphate buffer (pH 6.5) (hereinafter abbreviated as "buffer") containing 100 mM glycerol.

After washing the column with 150 mL of the buffer, enzymes were eluted with a linear gradient so as to attain the concentration of sodium chloride of 0.35 M in the buffer over 500 mL. Fractions (5 mL each) were collected and measured for ADH (1) activity and ALDH (2 and 3) activity according to the methods for activity measurement shown in Example 1.

Figure 8:
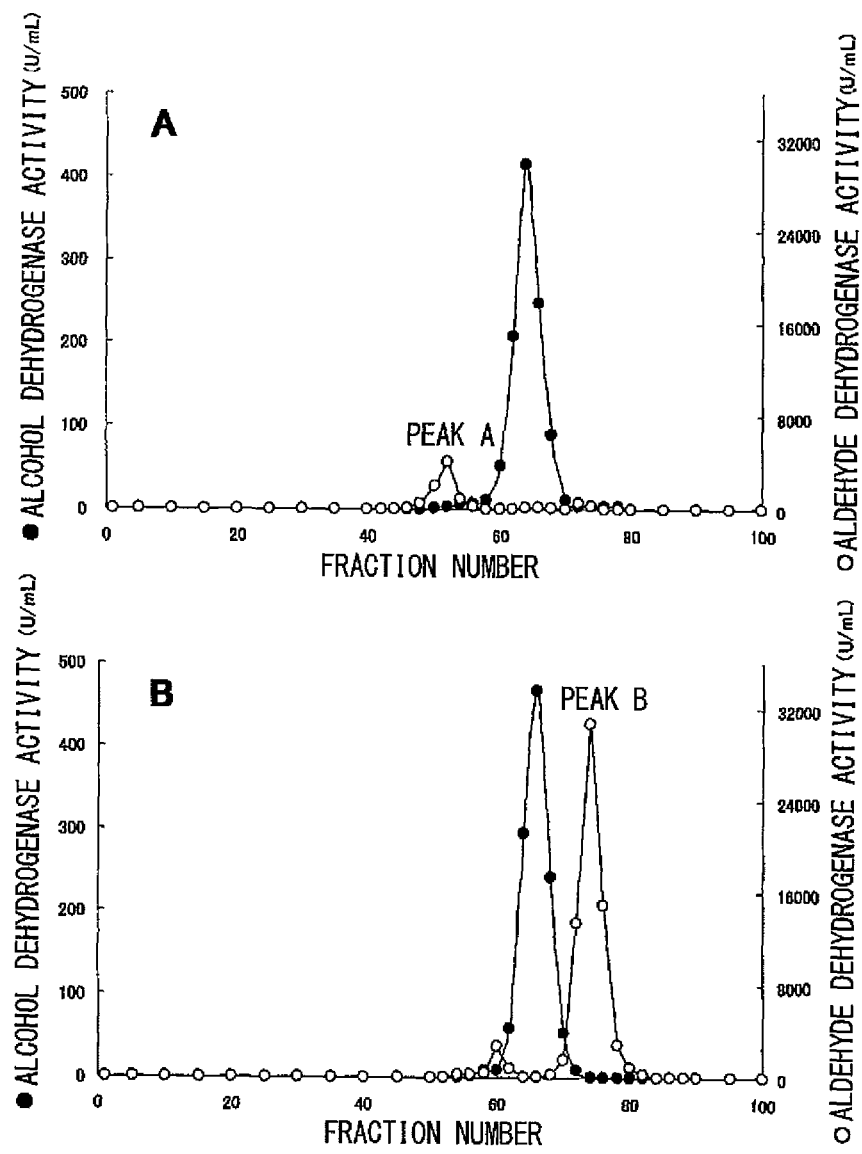
FIG. 8 shows elution patterns on ion exchange chromatography. A: Rh47-3 strain and B: K591s strain.

The elution pattern is shown in FIG. 8 (A: Rh47-3 strain, B: K591s strain). The peak having ADH (1) activity was eluted at almost the same position for both Rh47-3 and K591s strains. The fractions having ADH (1) activity were collected for each strain and were subjected to concentration and desalting with an ultrafiltration membrane having a molecular weight cut off of 10,000.

Meanwhile with regard to the peaks having ALDH (2 for Rh47-3 strain and 3 for K591s strain) activity, one peak was observed before the ADH (1) active fractions in Rh47-3 strain and two peaks were observed before and after the ADH (1) active fractions in K591s strain. Among these active peaks, fractions having high activities, namely fractions of peak A (Rh47-3 strain) and peak B (K591s strain) were collected and were subjected to concentration and desalting with an ultrafiltration membrane having a molecular weight cut off of 10,000. For both Rh47-3 and K591s strains, ALDH (3) activity was observed in non-adsorbed fractions. However because the enzyme activity was low, purification was not carried out.

(4) Hydrophobic Chromatography

To each fraction (about 3 mL) obtained by ion exchange chromatography, an equivalent amount of the buffer containing 3 M ammonium sulphate was added followed by centrifugation at 10,000 rpm for 20 minutes to remove insoluble substances. The obtained supernatant was applied to a column (inner diameter 3.0 cm×10 cm) containing TOYOPEARL Butyl-650 (Tosoh Corporation) which had been previously equilibrated with the buffer containing 1.5 M ammonium sulphate.

After washing the column with 100 mL of the buffer containing 1.5 M ammonium sulphate, adsorbed enzymes were eluted with a linear gradient so as to attain the concentration of ammonium sulphate of 0 M over 300 mL. Fractions having ADH (1) activity and ALDH (2 for Rh47-3 strain and 3 for K591s strain) activity were collected and were subjected to concentration and desalting with an ultrafiltration membrane having a molecular weight cut off of 10,000. For K591s strain, ALDH (3) activity was observed in non-adsorbed fractions. However because the enzyme activity was low, further purification was not carried out.

(5) Gel Filtration Chromatography

The fractions obtained by hydrophobic chromatography were subjected to a TSK-gel G3000SW column (inner diameter 6.0 mm×40 cm, Tosoh Corporation) which had been previously equilibrated with 10 mM phosphate buffer (pH 6.5) containing 0.1 M sodium chloride. Elution was carried out at a flow rate of 0.6 mL/min and detection was carried out with a UV detector (280 nm).

Accordingly PQQ-ADH (1) having ADH (1) activity was purified from Rh47-3 and K591s strains, PQQ-ALDH (2) having ALDH (2) activity was purified from Rh47-3 strain and PQQ/Heme-ALDH (4) having ALDH (3) activity was purified from K591s strain. The total activity, total amount of protein and specific activity of the purified enzymes is shown in Table 5.

TABLE 5

Total activity, total amount of protein and specific activity of purified enzymes

| | Enzyme | Total activity (U) | Total amount of protein (mg) | Specific activity (U/mg) |
|---|---|---|---|---|
| Rh47-3 strain | PQQ-ADH (1) | 2,054 | 53.2 | 38.6 |
| | PQQ-ALDH (2) | 22,320 | 2.5 | 8,928 |
| K591s strain | PQQ-ADH (1) | 1,408 | 39.1 | 36.0 |
| | PQQ/Heme-ALDH (4) | 132,775 | 4.8 | 27,661 |

Example 5

In the present Example, PQQ-ADH (1) was characterized.

ADH (1) enzymes purified respectively from *Pseudogluconobacter saccharoketogenes* Rh47-3 strain and *Pseudogluconobacter saccharoketogenes* K591s strain exhibited the identical properties and were identified as PQQ-ADH (1).

(1) Molecular Weight

Based on the result of SDS-PAGE analysis of the purified enzyme, it was determined that the enzyme had a molecular weight of 64,000±5,000. The molecular weight determined by gel filtration chromatography as described in Example 4 (5) was 120,000±10,000. Therefore it was predicted that the enzyme is a dimer of identical subunits.

(2) N-Terminal Amino Acid Sequence

After transferring the purified enzyme on a PVDF membrane, an N-terminal amino acid sequence of the enzyme was analyzed on an automated protein primary structure analyzer PPSQ-21A (Shimadzu Corporation). It was found that the amino acid sequence was Ala-Glu-Thr-Thr-Ser-Glu-Arg-Leu-Leu-Asn.

(3) Prosthetic Group

To a solution (50 μL) of the purified enzyme (360.0 μg), 50 μL of 1 N hydrochloric acid and 250 μL of methanol were added. The mixture was thoroughly mixed and then centrifuged at 12,000 rpm for 5 minutes. The supernatant (20 μL) thereof was analyzed by HPLC under the following conditions. Separately, 10 μL of 2 mM dithiothreitol (DTT) was added to 50 μL of the supernatant. The mixture was then analyzed by HPLC in the similar manner to examine whether or not the enzyme contained pyrroloquinoline quinone (PQQ).

Column: Cadenza CD-C18 (inner diameter 4.6 mm×7.5 cm, Imtakt Corporation)
Mobile phase: 30% (v/v) methanol containing 1% (v/v) of 85% phosphoric acid
Flow rate: 1.0 mL/min
Temperature: 35° C.
Detector: UV (254 nm)

As a result, the enzyme extract showed the same retention time as a standard PQQ (pyrroloquinoline quinone disodium salt, Kanto Chemical Co., Inc.). The enzyme extract after reducing treatment with DTT also had the same retention time as the standard PQQ after reducing treatment with DTT. From these results, it was suggested that PQQ-ADH (1) contains PQQ as a component.

(4) Optimal pH

Oxidation activity was measured in 0.15 M GTA buffer having pH ranging from 3.0 to 10.0. As a result, PQQ-ADH (1) had an optimal pH of 5.0 to 5.5.

(5) Substrate Specificity

Each substrate (D-glucose, sodium D-gluconate, sodium D-glucuronate, intermediate A, sodium salt of intermediate B) was dissolved in McIlvaine buffer (pH 5.0) and the activity of ADH was measured as described in Example 1 to study the substrate specificity of PQQ-ADH (1). The results are shown in Table 6. The enzyme activity for each substrate is expressed as a relative activity to the activity measured with D-glucose as a substrate that was set to be 100.

TABLE 6

Substrate specificity of PQQ-ADH (1)

| Substrate | Relative activity (%) |
|---|---|
| 0.2M D-glucose | 100 |
| 0.2M sodium D-gluconate | 88.6 |
| 0.2M sodium D-glucuronate | <1 |
| 0.02M intermediate A | 59.1 |
| 0.2M sodium salt of intermediate B | 2.7 |

(6) Analysis of Reaction Products

To each substrate solution (100 μL; 50 mM D-glucose, 50 mM sodium D-gluconate, 50 mM sodium D-glucuronate, 50 mM intermediate A or 50 mM sodium salt of intermediate B) containing 50 mM calcium carbonate, 90 μL of 100 mM potassium ferricyanide solution and 10 μL (46 U) of a solution of purified PQQ-ADH (1) were added and were subjected to the oxidation reaction that initiated at 30° C. The reaction products were quantified on the carbohydrate analysis system indicated in Example 1. The molar yield of the reaction products at 16 hours after the initiation of the reaction is shown in Table 7.

TABLE 7

Molar yield (%) of reaction products

| Substrate | D-glucose | D-gluconic acid | Intermediate A | Intermediate B | D-glucuronic acid | D-glucaric acid |
|---|---|---|---|---|---|---|
| D-glucose | 1.3 | 0 | 68.8 | 0 | 29.9 | 0 |
| Sodium D-gluconate | — | 22.6 | — | 77.4 | — | 0 |
| Sodium D-glucuronate | — | — | — | — | 100.0 | 0 |
| Intermediate A | — | — | 32.7 | 0.8 | 66.5 | 0 |
| Sodium salt of intermediate B | — | — | — | 97.9 | — | 2.1 |

Example 6

In the present Example, PQQ-ALDH (2) was characterized.

PQQ-ALDH (2) purified from *Pseudogluconobacter saccharoketogenes* Rh47-3 strain exhibited the following properties.

(1) Molecular Weight

From the result of SDS-PAGE analysis of a solution of the purified enzyme, it was determined that the enzyme had a molecular weight of 61,000±5,000. The molecular weight determined by gel filtration chromatography as described in Example 4 (5) was 180,000±10,000. Therefore it was predicted that the enzyme is a trimer of identical subunits.

(2) N-Terminal Amino Acid Sequence

After transferring the purified enzyme on a PVDF membrane, an N-terminal amino acid sequence of the enzyme was analyzed on an automated protein primary structure analyzer. However, the amino acid sequence could not be determined because the N-terminal was blocked.

(3) Internal Amino Acid Sequence

To 100 μL of a solution of the purified enzyme (220.8 μg), 10 μL of a V8 protease solution (0.1 mg of V8 protease dissolved in 1 mL of 0.1 M Tris-hydrochloric acid buffer (pH 8.0)) was added and was subjected to the reaction that allowed to proceed at 30° C. for 16 hours. Peptide fragments were separated by SDS-PAGE and transferred onto a PVDF membrane.

The internal amino acid sequence of the enzyme was analyzed on an automated protein primary structure analyzer and it was found that a peptide fragment having a molecular weight of 17 kDa had the amino acid sequence:

```
                                        (SEQ ID NO: 5)
Phe-Xaa-Ser-Asn-Thr-Asp-Val-Asn-Pro-Leu.
```

(4) Prosthetic Group

According to the result of the analysis carried out as the method described in Example 5 (3), it was suggested that PQQ-ALDH (2) contains PQQ as a component.

(5) Optimal pH

Oxidation activity was measured in GTA buffer having pH ranging from 4.0 to 10.0. As a result, PQQ-ALDH (2) had an optimal pH of 7.5 to 8.0.

(6) Substrate Specificity

Each substrate (D-glucose, sodium D-gluconate, sodium D-glucuronate, intermediate A, sodium salt of intermediate B, sodium glyoxylate) was dissolved in McIlvaine buffer (pH 8.0) and the activity of ALDH was measured as described in Example 1 to study the substrate specificity of PQQ-ALDH (2). The results are shown in Table 8. The enzyme activity for each substrate is expressed as a relative activity to the activity measured with the sodium salt of intermediate B as a substrate that was set to be 100.

TABLE 8

Substrate specificity of PQQ-ALDH (2)

| Substrate | Relative activity (%) |
|---|---|
| 0.2M D-glucose | 11.8 |
| 0.2M sodium D-gluconate | <1 |
| 0.2M sodium D-glucuronate | 18.6 |
| 0.02M intermediate A | 476 |
| 0.2M sodium salt of intermediate B | 100 |
| 0.2M sodium glyoxylate | 3,050 |

(7) Analysis of Reaction Products

To each substrate solution (100 μL; 50 mM D-glucose, 50 mM sodium D-gluconate, 50 mM sodium D-glucuronate, 50 mM intermediate A or 50 mM sodium salt of intermediate B) containing 50 mM calcium carbonate, 90 μL of 100 mM potassium ferricyanide solution and 10 μL (188 U) of a solution of purified PQQ-ALDH (2) were added and were subjected to the oxidation reaction that initiated at 30° C. The reaction products were quantified on the carbohydrate analysis system indicated in Example 1. The molar yield of the reaction products at 16 hours after the initiation of the reaction is shown in Table 9.

TABLE 9

Molar yield (%) of reaction products

| Substrate | D-glucose | D-gluconic acid | Intermediate A | Intermediate B | D-glucuronic acid | D-glucaric acid |
|---|---|---|---|---|---|---|
| D-glucose | 97.8 | 2.2 | 0 | 0 | 0 | 0 |
| Sodium D-gluconate | — | 100.0 | — | 0 | — | 0 |
| Sodium D-glucuronate | — | — | — | — | 93.5 | 6.5 |
| Intermediate A | — | — | 0.8 | 23.4 | 59.8 | 16.0 |
| Sodium salt of intermediate B | — | — | — | 67.7 | — | 32.3 |

Example 7

In the present Example, PQQ/Heme-ALDH (4) was characterized.

PQQ/Heme-ALDH (4) purified from *Pseudogluconobacter saccharoketogenes* K591s strain exhibited the following properties.

(1) Molecular Weight

From the result of SDS-PAGE analysis of a solution of the purified enzyme, it was determined that the enzyme had a molecular weight of 59,000±5,000. The molecular weight determined by gel filtration chromatography under the conditions described in Example 4 (5) was 130,000±10,000. Therefore it was predicted that the enzyme is a dimer of identical subunits.

(2) N-Terminal Amino Acid Sequence

After transferring the purified enzyme on a PVDF membrane, an N-terminal amino acid sequence of the enzyme was analyzed on an automated protein primary structure analyzer. However, the amino acid sequence could not be determined because the N-terminal was blocked.

(3) Internal amino acid sequence

To 100 μL of a solution of the purified enzyme (200.5 μg), 10 μL of a V8 protease solution (0.1 mg of V8 protease dissolved in 1 mL of 0.1 M Tris-hydrochloric acid buffer (pH 8.0)) was added and was subjected to the reaction that allowed to proceed at 27° C. for 16 hours. Peptide fragments were separated by SDS-PAGE and transferred onto a PVDF membrane. The internal amino acid sequence of the enzyme was analyzed on an automated protein primary structure analyzer and it was found that a peptide fragment having a molecular weight of 37 kDa had the amino acid sequence:

```
                                              (SEQ ID NO: 6)
   Ala-Ser-Trp-Asn-Gly-Val-Pro-Pro-Glu-Asn.
```

(4) Prosthetic Group

According to the result of the analysis carried out as the method described in Example 5 (3), it was suggested that PQQ/Heme-ALDH (4) contains PQQ as a component. Separately a solution of the purified enzyme (100.4 μg/mL) was added with 1/20 amount of 1M Tris-hydrochloric acid buffer (pH 9.0) followed by addition of sodium dithionite up to a final concentration of 5 mM. The absorption spectrum of the solution was measured. The result showed the absorption maximum at 522 and 550 nm, and thus it was suggested that PQQ/Heme-ALDH (4) contains, in addition to PQQ, Heme c as a prosthetic group.

(5) Optimal pH

Oxidation activity was measured in GTA buffer having pH ranging from 4.0 to 10.0. As a result, PQQ-ALDH (4) had an optimal pH of 7.5 to 8.0.

(6) Substrate Specificity

Each substrate (D-glucose, sodium D-gluconate, sodium D-glucuronate, intermediate A, sodium salt of intermediate B, sodium glyoxylate) was dissolved in McIlvaine buffer (pH 8.0) and the activity of ALDH was measured as described in Example 1 to study the substrate specificity of PQQ/Heme-ALDH (4). The results are shown in Table 10. The enzyme activity for each substrate is expressed as a relative activity to the activity measured with sodium D-gluconate as a substrate that was set to be 100.

TABLE 10

| Substrate specificity of PQQ/Heme-ALDH (4) | |
| --- | --- |
| Substrate | Relative activity (%) |
| 0.2M D-glucose | 35.1 |
| 0.2M sodium D-gluconate | 100 |
| 0.2M sodium D-glucuronate | 2.9 |
| 0.02M intermediate A | 11.6 |
| 0.2M sodium salt of intermediate B | 21.1 |
| 0.2M sodium glyoxylate | 20,260 |

(7) Analysis of Reaction Products

To each substrate solution (100 μL; 50 mM D-glucose, 50 mM sodium D-gluconate, 50 mM sodium D-glucuronate, 50 mM intermediate A or 50 mM sodium salt of intermediate B) containing 50 mM calcium carbonate, 90 μL of 100 mM potassium ferricyanide solution and 10 μL (1,680 U) of a solution of purified PQQ/Heme-ALDH (4) were added and was subjected to the oxidation reaction that initiated at 30° C. The reaction products were quantified on the carbohydrate analysis system indicated in Example 1. The molar yield of the reaction products at 16 hours after the initiation of the reaction is shown in Table 11. A slight amount of D-glucaric acid was produced only when sodium D-glucuronate was used as a substrate.

TABLE 11

| | Molar yield (%) of reaction products | | | | | | | |
| --- | --- | --- | --- | --- | --- | --- | --- | --- |
| Substrate | D-glucose | D-gluconic acid | Intermediate A | Intermediate B | 2-keto-D-gluconic acid | D-glucuronic acid | D-glucaric acid | Other substances |
| D-glucose | 22.4 | 0.8 | 0 | 0 | 72.1 | 0 | 0 | 4.7 |
| Sodium D-gluconate | — | 0 | — | 0 | 84.8 | — | 0 | 15.2 |
| Sodium D-glucuronate | — | — | — | — | — | 94.1 | 5.3 | 0.6 |
| Intermediate A | — | — | 69.6 | 12.0 | — | 0 | 0 | 18.4 |
| Sodium salt of intermediate B | — | — | — | 58.1 | — | 0 | 0 | 41.9 |

Example 8

In the present Example, the purified enzymes were used for production of D-glucaric acid.

To each substrate solution (100 μL; 50 mM D-glucose, 50 mM sodium D-gluconate, 50 mM sodium D-glucuronate) containing 50 mM calcium carbonate, 90 μL of 100 mM potassium ferricyanide solution and 5 μL of a solution of a purified enzyme (PQQ-ADH (1): 23 U, PQQ-ALDH (2): 94 U or PQQ/Heme-ALDH (4): 840 U) or pure water were added and were subjected to the reaction that carried out at 30° C. for 36 hours. The produced D-glucaric acid or 2-keto-D-gluconic acid were quantified on the carbohydrate analysis system indicated in Example 1.

The results are shown in Table 12. The combination of PQQ-ADH (1) and PQQ-ALDH (2) produced D-glucaric acid from D-glucose or D-gluconic acid. The combination of PQQ-ADH (1) and PQQ/Heme-ALDH (4) did not produce D-glucaric acid but mainly produced 2-keto-D-gluconic acid from D-glucose or D-gluconic acid.

TABLE 12

| Reactions for producing D-glucaric acid and 2-keto-D-gluconic acid using purified enzymes | | | |
| --- | --- | --- | --- |
| | | Yield (mM) | |
| Substrate | Reaction condition | D-glucaric acid | 2-keto-D-gluconic acid |
| D-glucose | PQQ-ADH (1) + pure water | 0 | 0 |
| | PQQ-ALDH (2) + pure water | 0 | 0 |
| | PQQ-ADH (1) + PQQ-ALDH (2) | 12.8 | 0 |

TABLE 12-continued

Reactions for producing D-glucaric acid and
2-keto-D-gluconic acid using purified enzymes

| | | Yield (mM) | |
|---|---|---|---|
| Substrate | Reaction condition | D-glucaric acid | 2-keto-D-gluconic acid |
| | PQQ-ADH (1) + PQQ/Heme-ALDH (4) | 0 | 18.3 |
| Sodium D-gluconate | PQQ-ADH (1) + pure water | 0 | 0 |
| | PQQ-ALDH (2) + pure water | 0 | 0 |
| | PQQ-ADH (1) + PQQ-ALDH (2) | 21.7 | 0 |
| | PQQ-ADH (1) + PQQ/Heme-ALDH (4) | 0 | 24.1 |
| Sodium D-glucuronate | PQQ-ADH (1) + pure water | 0 | 0 |
| | PQQ-ALDH (2) + pure water | 2.8 | 0 |
| | PQQ-ADH (1) + PQQ-ALDH (2) | 2.5 | 0 |
| | PQQ-ADH (1) + PQQ/Heme-ALDH (4) | 3.3 | 0 |

Example 9

In the present Example, analysis of the draft genome of *Pseudogluconobacter saccharoketogenes* Rh47-3 strain was carried out.

Genomic DNA was recovered from cultivated cells of *Pseudogluconobacter saccharoketogenes* Rh47-3 strain using GenElute™ Bacterial Genomic DNA kit (SIGMA). The genomic DNA was fragmented to respectively have a size of about 500 by and a biotinylated adaptor was ligated to each fragment. Single-stranded DNA was recovered with streptavidin magnetic beads and the size and concentration of DNA were detected on Bioanalyzer 2100 (Agilent).

Single-stranded DNA was mixed with beads onto which a complementary sequence of the adaptor was immobilized and subjected to emulsion PCR. After PCR, an appropriate amount of beads were added to a plate and the base sequence was analyzed by pyrosequencing using GS Titanium Sequencing kit XLR70 and Genome Sequencer FLX System (Roche Diagnostics).

The results showed that the number of total bases analyzed were 106,737,181 bases, the number of contigs of 4 kbase or more was 20 and the number of total bases in contigs of 4 kbase or more was 3,875,227 bases.

The base sequence analyzed contained 4,345 predicted amino acid coding regions, among which 273 coding regions had homology with dehydrogenases based on homology search. These predicted amino acid sequences included the sequences which matched with the N-terminal amino acid sequence of PQQ-ADH (1), the internal amino acid sequence of PQQ-ALDH (2) and the internal amino acid sequence of PQQ/Heme-ALDH (4) respectively revealed in Examples 5, 6 and 7.

Example 10

In the present Example, the base sequences of PQQ-ADH (1), PQQ-ALDH (2) and PQQ/Heme-ALDH (4) genes were determined.

Primers were designed by using genomic DNAs of *Pseudogluconobacter saccharoketogenes* Rh47-3 and K591s strains as templates and based on information of the base sequence of the draft analysis obtained in Example 9.

The designed primers (PQQ-ADH (1) forward primer: SEQ ID NO: 4, PQQ-ADH (1) reverse primer: SEQ ID NO: 5, PQQ-ALDH (2) forward primer: SEQ ID NO: 6, PQQ-ALDH (2) reverse primer: SEQ ID NO: 7, PQQ/Heme-ALDH (4) forward primer: SEQ ID NO: 8, PQQ/Heme-ALDH (4) reverse primer: SEQ ID NO: 9) and Pfx50 DNA polymerase (Life Technologies) were used in PCR to determine base sequences of gene regions of PQQ-ADH (1), PQQ-ALDH (2) and PQQ/Heme-ALDH (4) of Rh47-3 and K591s strains.

The base sequence and a predicted amino acid sequence of PQQ-ADH (1) gene derived from Rh47-3 strain are shown in SEQ ID NO: 1. PQQ-ADH (1) gene contains 1,800 by (599 amino acid residues) and the amino acid sequence thereof has 42% homology with quinoprotein ethanol dehydrogenase derived from *Bradyrhizobium* sp. PQQ-ADH (1) gene derived from K591s strain had an identical sequence as PQQ-ADH (1) gene derived from Rh47-3 strain.

The base sequence and a predicted amino acid sequence of PQQ-ALDH (2) gene derived from Rh47-3 strain are shown in SEQ ID NO: 2. PQQ-ALDH (2) gene contains 1,761 by (586 amino acid residues) and the amino acid sequence thereof has 35% homology with methanol dehydrogenase large subunit protein derived from *Pelagibacterium halotolerans*.

PQQ-ALDH (2) gene derived from K591s strain had the base sequence wherein the 1533rd base, A, in the base sequence of PQQ-ALDH (2) gene derived from Rh47-3 strain was replaced by G, which, however, gave the same translated amino acid, leucine (Leu).

The base sequence and a predicted amino acid sequence of PQQ/Heme-ALDH (4) derived from Rh47-3 strain is shown in SEQ ID NO: 3. PQQ/Heme-ALDH (4) gene contains 1785 by (594 amino acid residues) and the amino acid sequence thereof has 41% homology with methanol dehydrogenase large subunit protein derived from *Pelagibacterium halotolerans*.

PQQ/Herne-ALDH (4) gene derived from K591s strain had the base sequence wherein the 224th base, T, in the base sequence of PQQ/Heme-ALDH (4) gene derived from Rh47-3 strain was replaced by C, which gave the amino acid threonine (Thr) instead of isoleucine (Ile).

Example 11

In the present Example, large scale production of D-glucaric acid from D-glucose was carried out.

According to the method described in Example 4, *Pseudogluconobacter saccharoketogenes* Rh47-3 strain was cultivated in the scale of 30 L. The cells collected by centrifugation (6,000 rpm, 20 minutes) were added to 30 L of 10 g/L D-glucose solution and were subjected to the reaction that carried out under the conditions of a temperature of 30° C., a stirring speed of 150 rpm, aeration of 10 L/min. During the reaction, pH was adjusted to 7.0 with 12% (w/v) sodium hydroxide solution.

Figure 9:
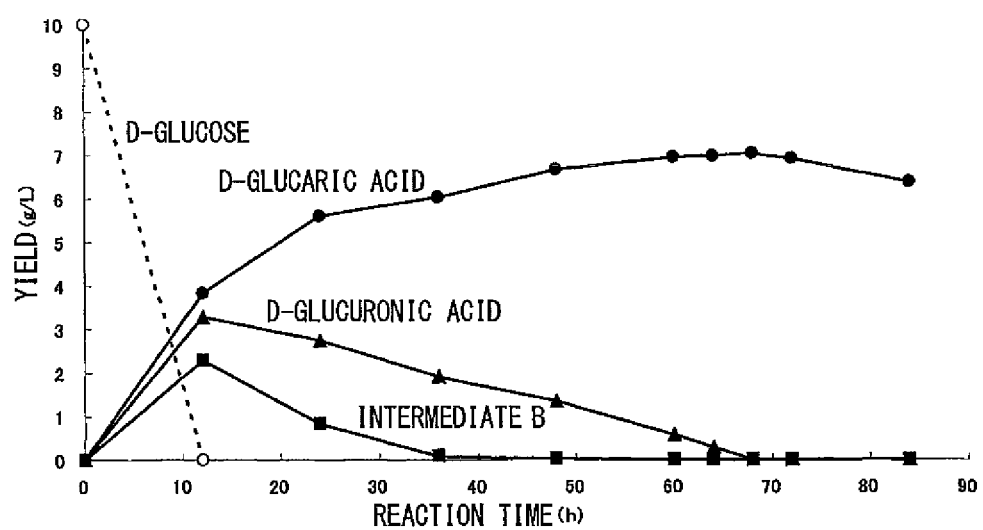
FIG. 9 shows a profile over time of oxidation reaction with a substrate D-glucose.

Samples were taken over time and quantified for generated D-glucaric acid on the carbohydrate analysis system indicated in Example 1. The results show, as shown in FIG. 9, that 7.0 g/L (molar yield: 60.3%) of D-glucaric acid was produced at maximum at 68 hours after initiation of the reaction.

Example 12

In the present Example, large scale production of D-glucaric acid from sodium D-gluconate was carried out.

According to the method described in Example 2, *Pseudogluconobacter saccharoketogenes* Rh47-3 strain was cultivated in the scale of 30 L. The cells collected by centrifugation (6,000 rpm, 20 minutes) were added to 30 L of 30 g/L sodium D-gluconate solution and were subjected to the reaction that carried out under the conditions of a temperature of 30° C., a stirring speed of 150 rpm, aeration of 10 L/min.

Figure 10:
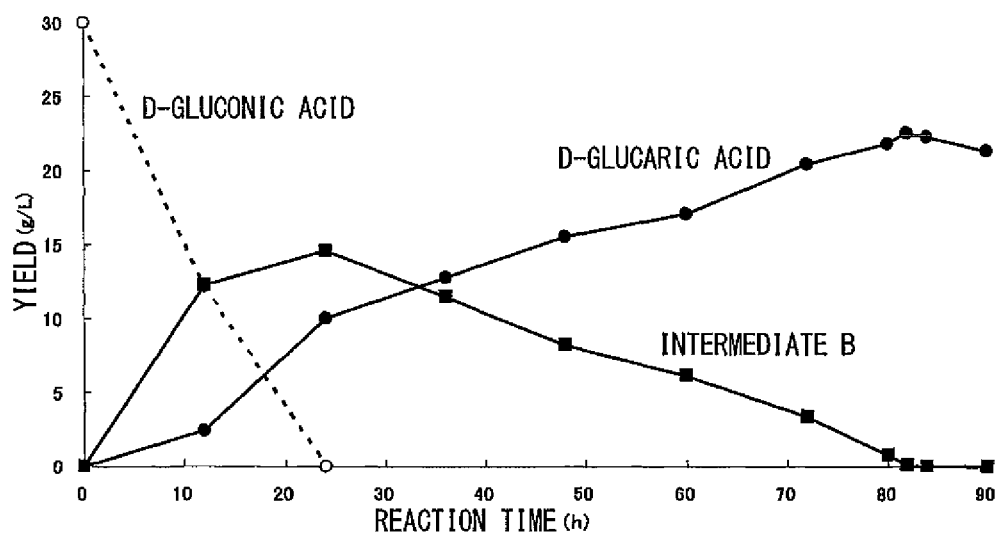
FIG. 10 shows a profile over time of oxidation reaction with a substrate sodium D-gluconate.

During the reaction, pH was adjusted to 7.0 with 12% (w/v) sodium hydroxide solution. Samples were taken over time and quantified for generated D-glucaric acid on the carbohydrate analysis system indicated in Example 1. The results show, as shown in FIG. 10, that 22.5 g/L (molar yield: 78.6%) of D-glucaric acid was produced at maximum at 82 hours after initiation of the reaction.

Example 13

In the present Example, the purified enzyme was used for production of D-glucaraldehyde (intermediate A).

To a substrate solution (100 µL; 50 mM D-glucose) containing 50 mM calcium carbonate, 90 µL of 100 mM potassium ferricyanide solution and 10 µL of a solution of purified PQQ-ADH (1) (46 U) were added and were subjected to the oxidation reaction that initiated at 30° C. The reaction products were quantified on the carbohydrate analysis system indicated in Example 1. At 16 hours after initiation of the reaction, D-glucaraldehyde (intermediate A) was produced at a molar yield of 68.8%.

Example 14

In the present Example, the purified enzyme was used for production of L-guluronic acid (intermediate B).

To a substrate solution (100 µL; 50 mM sodium D-gluconate) containing 50 mM calcium carbonate, 90 µL of 100 mM potassium ferricyanide solution and 10 µL of a solution of purified PQQ-ADH (1) (46 U) were added and were subjected to the oxidation reaction that initiated at 30° C. The reaction products were quantified on the carbohydrate analysis system indicated in Example 1. At 16 hours after initiation of the reaction, L-guluronic acid (intermediate B) sodium salt was produced at a molar yield of 77.4%.

Example 15

In the present Example, large scale production of L-guluronic acid (intermediate B) from D-glucose was carried out.

According to the method described in Example 4, *Pseudogluconobacter saccharoketogenes* Rh47-3 strain was cultivated in the scale of 30 L. The cells collected by centrifugation (6,000 rpm, 20 minutes) were added to 30 L of 10 g/L D-glucose solution and were subjected to the reaction that carried out under the conditions of a temperature of 30° C., a stirring speed of 150 rpm, aeration of 10 L/min.

During the reaction, pH was adjusted to 7.0 with 12% (w/v) sodium hydroxide solution. Samples were taken over time and quantified for generated L-guluronic acid on the carbohydrate analysis system indicated in Example 1. The results show that 2.2 g/L (molar yield: 18.3%) of L-guluronic acid (intermediate B) sodium salt was produced at maximum at 12 hours after initiation of the reaction.

Example 16

In the present Example, large scale production of L-guluronic acid (intermediate B) from sodium D-gluconate was carried out.

According to the method described in Example 4, *Pseudogluconobacter saccharoketogenes* Rh47-3 strain was cultivated in the scale of 30 L. The cells collected by centrifugation (6,000 rpm, 20 minutes) were added to 30 L of 30 g/L sodium D-gluconate solution and were subjected to the reaction that carried out under the conditions of a temperature of 30° C., a stirring speed of 150 rpm, aeration of 10 L/min.

During the reaction, pH was adjusted to 7.0 with 12% (w/v) sodium hydroxide solution. Samples were taken over time and quantified for generated L-guluronic acid on the carbohydrate analysis system indicated in Example 1. The results show that 14.9 g/L (molar yield: 41.3%) of L-guluronic acid (intermediate B) sodium salt was produced at maximum at 24 hours after initiation of the reaction.

INDUSTRIAL APPLICABILITY

As specifically described above, the present invention relates to a D-glucaric acid producing bacterium and a method for producing D-glucaric acid. According to the present invention, a microorganism having improved productivity of D-glucaric acid can be provided. In addition, by using the microorganism having improved productivity of D-glucaric acid, D-glucaric acid can be inexpensively and effectively produced and provided. A method for producing D-glucaraldehyde (intermediate A) and L-guluronic acid (intermediate B) can also be provided which are intermediates during production of D-glucaric acid. Further alcohol dehydrogenase ADH (1) having the amino acid sequence of SEQ ID NO: 1 or an amino acid sequence having 80% or higher homology therewith and aldehyde dehydrogenase ALDH (2) having the amino acid sequence of SEQ ID NO: 2 or an amino acid sequence having 80% or higher homology therewith can be provided. The present invention is useful because it can provide a novel technique with regard to a microorganism having improved productivity of D-glucaric acid to be used for production of D-glucaric acid and a method for efficiently producing D-glucaric acid.

Reference to Deposited Microorganism
Name of international depositary institution: International Patent Organism Depositary, National Institute of Technology and Evaluation
Address of international depositary institution: #120, 2-5-8, Kazusakamatari, Kisarazu-shi, Chiba, 292-0818 Japan
Date of Acceptance: 26 Apr. 2007
Accession Number: FERM BP-10820
Indication of Microorganism: Rh47-3

The invention claimed is:

1. A method for producing D-glucaric acid or a salt thereof, which comprises mixing
   (i) an isolated alcohol dehydrogenase ADH (1); and
   (ii) an isolated aldehyde dehydrogenase ALDH (2)
in an aqueous solution of one or more saccharides selected from the group consisting of D-glucose, D-gluconic acid, and L-guluronic acid, whereby C1 aldehyde residue of D-glucose is specifically oxidized, and then C6 hydroxymethyl residue of D-gluconic acid is specifically oxidized to form D-glucaric acid without generating D-glucaraldehyde or D-glucuronic acid, to progress the following enzymatic reactions to generate the D-glucaric acid or the salt thereof, D-glucose→D-gluconic acid→L-guluronic acid→D-glucaric acid
(Intermediate B)

wherein said isolated alcohol dehydrogenase ADH (1) comprises a pyrroloquinoline quinone-dependent enzyme PQQ-ADH (1) having a molecular weight of 64,000±5,000 as measured by SDS-PAGE and a molecular weight of 120,000±10,000 as measured by gel filtration chromatography and comprises the amino acid sequence represented by SEQ ID NO: 1, and
   wherein said isolated aldehyde dehydrogenase ALDH (2) comprises a pyrroloquinoline quinone-dependent enzyme PQQ-ALDH (2) having a molecular weight of 61,000±5,000 as measured by SDS-PAGE and a molecular weight of 180,000±10,000 as measured by gel filtration chromatography and comprises the amino acid sequence represented by SEQ ID NO: 2, and
   recovering the D-glucaric acid or the salt thereof resulting therefrom.

2. The method according to claim 1, wherein the isolated alcohol dehydrogenase ADH (1) is encoded by a nucleic acid molecule comprising SEQ ID NO: 7.

3. The method according to claim 1, wherein the isolated aldehyde dehydrogenase ALDH (2) is encoded by a nucleic acid molecule comprising SEQ ID NO: 8.

4. The method according to claim 1, wherein L-guluronic acid (intermediate B) is produced in the presence of D-glucose, D-gluconic acid, or both.

5. The method according to claim 1, which further comprises adjusting the pH of the reaction mixture to be in the range of 5 to 8.

6. The method according to claim 1, which further comprises adjusting the concentration of D-glucose in the reaction mixture to 1 to 2% (w/v).

7. The method according to claim 1, wherein the isolated alcohol dehydrogenase ADH (1) is obtained from the strain of Pseudogluconobacter saccharoketogenes Rh47-3 (FERM BP-10820).

8. The method according to claim 1, wherein the isolated aldehyde dehydrogenase ALDH (2) is obtained from the strain of Pseudogluconobacter saccharoketogenes Rh47-3 (FERM BP-10820).

* * * * *